United States Patent
Yagi et al.

(10) Patent No.: US 11,166,436 B2
(45) Date of Patent: Nov. 9, 2021

(54) HEALTH CONDITION ESTIMATION DEVICE

(71) Applicant: OSAKA UNIVERSITY, Osaka (JP)

(72) Inventors: Yasushi Yagi, Osaka (JP); Fumio Okura, Osaka (JP); Yasushi Makihara, Osaka (JP); Daigo Muramatsu, Osaka (JP)

(73) Assignee: OSAKA UNIVERSITY, Osaka (JP)

( * ) Notice: Subject to any disclaimer, the term of this patent is extended or adjusted under 35 U.S.C. 154(b) by 267 days.

(21) Appl. No.: 16/097,557

(22) PCT Filed: Feb. 13, 2017

(86) PCT No.: PCT/JP2017/005089
§ 371 (c)(1),
(2) Date: Oct. 29, 2018

(87) PCT Pub. No.: WO2017/187719
PCT Pub. Date: Nov. 2, 2017

(65) Prior Publication Data
US 2019/0150405 A1    May 23, 2019

(30) Foreign Application Priority Data
Apr. 28, 2016    (JP) .............................. JP2016-090680

(51) Int. Cl.
*A01K 29/00* (2006.01)
*A61B 5/107* (2006.01)
(Continued)

(52) U.S. Cl.
CPC ............ *A01K 29/005* (2013.01); *A01K 29/00* (2013.01); *A61B 5/107* (2013.01); *A61B 5/11* (2013.01); *G16H 50/30* (2018.01); *G16H 30/40* (2018.01)

(58) Field of Classification Search
CPC .... A01K 29/00; A01K 29/005; A01K 11/006; A01K 15/027; A61B 5/107; A61B 5/11;
(Continued)

(56) References Cited

U.S. PATENT DOCUMENTS 7,039,220 B2 *   5/2006   Kriesel ................. G01B 11/25
                                                              382/110
7,399,220 B2 *   7/2008   Kriesel ................ A01K 11/008
                                                              452/157
(Continued)

FOREIGN PATENT DOCUMENTS

CA       2944395 A1 * 10/2015 ............... G06T 7/60
JP       2006218122      8/2006
(Continued)

OTHER PUBLICATIONS

"Depth-based gait feature representation.", H. Nakajima, I. Mitsugami, Y. Yagi, IPSJ Trans. on Computer Vision and Applications, vol. 5, pp. 94-98, 2013.
(Continued)

*Primary Examiner* — Ebony E Evans
(74) *Attorney, Agent, or Firm* — Stephen J. Weyer, Esq.; Stites & Harbison PLLC

(57) ABSTRACT

A health condition estimation device capable of accurately estimating the health condition of a cow includes: a three-dimensional coordinates acquisition unit which acquires a group of three-dimensional coordinates representing the three-dimensional shape of a cow extracted from a distance image of the cow; a feature amount extraction unit which extracts the feature amount of the cow according to the group of three-dimensional coordinates acquired by the three-dimensional coordinates acquisition unit; and a score calculation unit which calculates a score that indicates the health condition of the cow, according to the feature amount extracted by the feature amount extraction unit. It is pref-
(Continued)

erable: that the feature amount extraction unit extracts the feature amount that indicates the degree of sinking of the rumen, according to a group of three-dimensional coordinates in a rumen area in the group of three-dimensional coordinates acquired by the three-dimensional coordinates acquisition unit, the rumen area being an area on the body surface of the cow proximal to the rumen; and that the score calculation unit calculates the cow rumen fill score according to the feature amount extracted by the feature amount extraction unit and representing the degree of sinking of the rumen.

13 Claims, 13 Drawing Sheets

(51) Int. Cl.
  *A61B 5/11* (2006.01)
  *G16H 50/30* (2018.01)
  *G16H 30/40* (2018.01)

(58) Field of Classification Search
  CPC ..... A61B 5/112; A61B 5/1072; A61B 5/1121; A61B 5/1122; A61B 5/1123; A61B 5/1073; A61B 5/1075; G16H 50/20; G16H 50/30
  USPC ........................................................ 119/421
  See application file for complete search history.

(56) References Cited

U.S. PATENT DOCUMENTS

| | | | | |
|---|---|---|---|---|
| 8,659,764 | B2* | 2/2014 | Hatzilias | G06T 7/60 356/601 |
| 9,142,028 | B2* | 9/2015 | Banhazi | G06T 7/60 |
| 9,675,253 | B2 | 6/2017 | Granz et al. | |
| 9,684,956 | B2* | 6/2017 | Liao | G06T 7/0012 |
| 2008/0021352 | A1* | 1/2008 | Keegan | A61B 5/1038 600/595 |
| 2009/0099457 | A1* | 4/2009 | Barnes | G16H 30/20 600/476 |
| 2009/0299232 | A1* | 12/2009 | Lanfermann | G06K 9/00342 600/595 |
| 2012/0000300 | A1* | 1/2012 | Sunagawa | A61B 5/4023 73/865.4 |
| 2014/0180130 | A1 | 6/2014 | Granz et al. | |
| 2016/0012278 | A1* | 1/2016 | Banhazi | G06K 9/46 382/110 |
| 2017/0243354 | A1* | 8/2017 | Tafazzoli | A61B 5/7275 |
| 2019/0069512 | A1* | 3/2019 | Eriksson | A01K 29/005 |
| 2020/0060240 | A1* | 2/2020 | Yajima | A01K 29/00 |
| 2020/0143157 | A1* | 5/2020 | Borchersen | G06K 9/00362 |
| 2021/0085240 | A1* | 3/2021 | Pena | G06K 9/52 |

FOREIGN PATENT DOCUMENTS

| | | |
|---|---|---|
| JP | 2015173732 | 10/2015 |
| JP | 2016/059300 | 4/2016 |
| WO | WO-2012138290 A1 * | 10/2012 ........... A61B 5/4238 |

OTHER PUBLICATIONS

Okada, K., et al. "Detection of Hoof Diseases in Cattle Using a Triaxial Accelerometer." *Japanese Journal of Large Animal Clinics*, vol. 2, No. 4, 2011, pp. 183-188., doi:10.4190/jjlac.2.183.
Schlageter-Tello, Andrés, et al. "Manual and Automatic Locomotion Scoring Systems in Dairy Cows: A Review." *Preventive Veterinary Medicine*, vol. 116, No. 1-2, 2014, pp. 12-25., doi:10.1016/j.prevetmed.2014.06.006.
"Three-dimensional walking image analysis for detection of hooves disease in dairy cattle," Shoya, et al, Information Processing Society Research Report, IPSJ SIG Technical Report.
S.Viazzi, Comparison of a three-dimensional and two-dimensional camera system for automated measurement of back posture in dairy cows, Computers and Electronics in Agriculture, 2014, vol. 100, p. 139-147.
Tamaki Kida, "A Technique for Measuring Grazing Cattle Form Using a 3D Digital Camera", Journal of Japanese Society of Grassland Science, 2014, vol. 60, No. 2, pp. 85 to 90.
T.Van Hertem, Comparison of segmentation algorithms for cow contour extraction from natural barn background in side view images, Computers and Electronics in Agriculture, 2013, vol. 91, p. 65-74.
"Person re-identification using view-dependent score-level fusion of gait and color features.", R. Kawai, Y. Makihara, C. Hua, H. Iwama, Y. Yagi, Proc. 21st International Conference on Pattern Recognition (ICPR), pp. 2694-2697, 2012.
Poursaberi, A., et al. "Real-Time Automatic Lameness Detection Based on Back Posture Extraction in Dairy Cattle: Shape Analysis of Cow with Image Processing Techniques." Computers and Electronics in Agriculture, vol. 74, No. 1, 2010, pp. 110-119., doi:10.1016/j.compag.2010.07.004.
"Individual recognition using gait energy image.", J. Han, B. Bhanu, IEEE Transactions on Pattern Analysis and Machine Intelligence, 28(2), pp. 316-322, 2006.
Automatic lameness detection based on consecutive 3D-video recordings (Feb. 25, 2014), Biosystems Engineering, vol. 119, pp. 108-116. T. Van Hertem, S. Viazzi, M. Steensels, et al.
"Clothing-invariant gait identification using part-based clothing categorization and adaptive weight control.", M. Hossain, Y. Makihara, J. Wang, Y. Yagi, Pattern Recognition, 43(6) pp. 2281-2291, 2010.
"Construction of walking image database of dairy cattle and individual identification," Ikuma, et al., The 18th Symposium on Image Recognition and Understanding.
"Individual identification based on construction of video database of dairy cattle and image analysis," Ikuma, et al., Information Processing Society Research Report, IPSJ SIG Technical Report.
International Search Report for PCT/JP2017/005089, dated Apr. 11, 2017.
Written Opinion of the International Search Authority for PCT/JP2017/005089, dated Mar. 31, 2017.
Anonymous: "Cow and gait: 3D monitoring of animal health could reduce stock losses—UWE Bristol: New Releases", Feb. 6, 2014, XP055666270.
Hansen, Mark, et al., "Non-intrusive automated measurement of dairy cow body condition using 3D video", Procedings of the Machine Vision of Animals and Their Behaviour Workshop 2015, Sep. 10, 2015, pp. 1.1-1.8, XP055666257, DOI: 10.5244/C.29.MVAB.1; ISBN: 978-10901725-57-5.
European Examination Report dated Feb. 18, 2020 in European Patent Application No. 17789008.4.

* cited by examiner

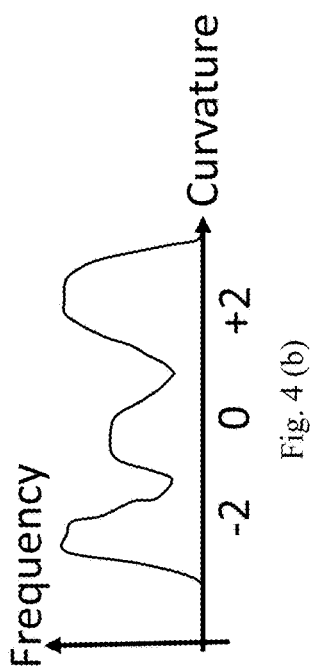
Fig. 4(a)
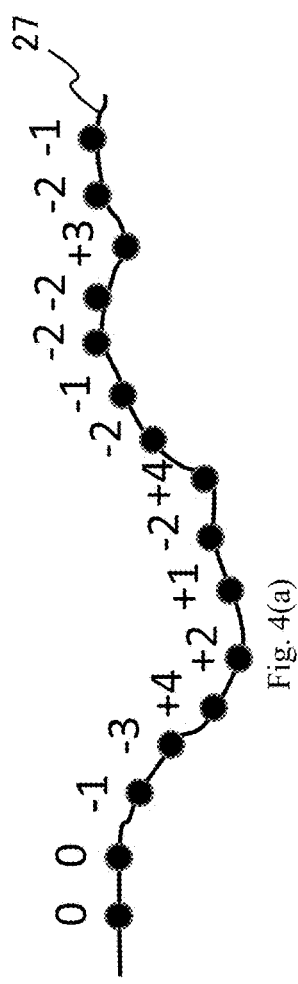
Fig. 4(b)
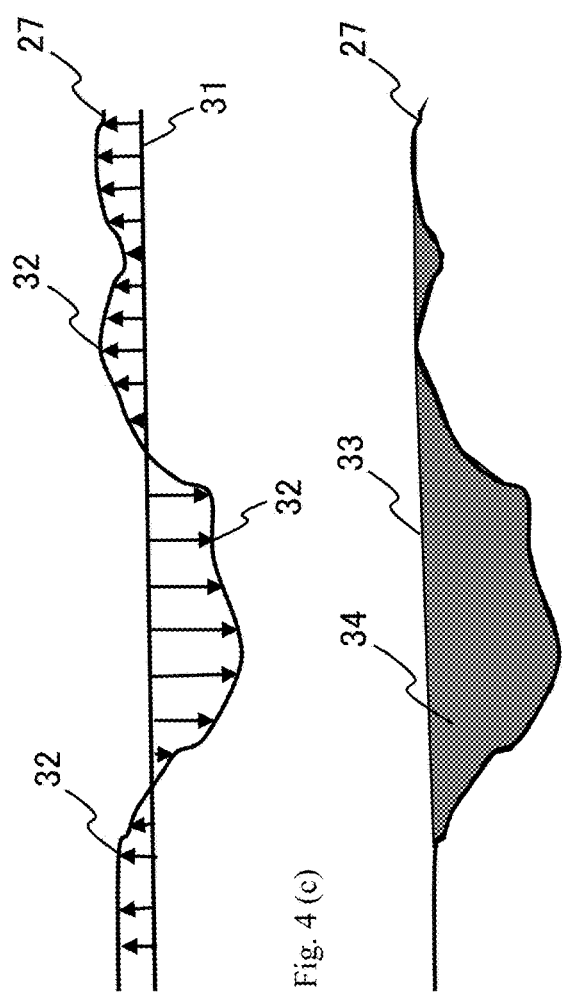
Fig. 4(c)
Fig. 4(d)

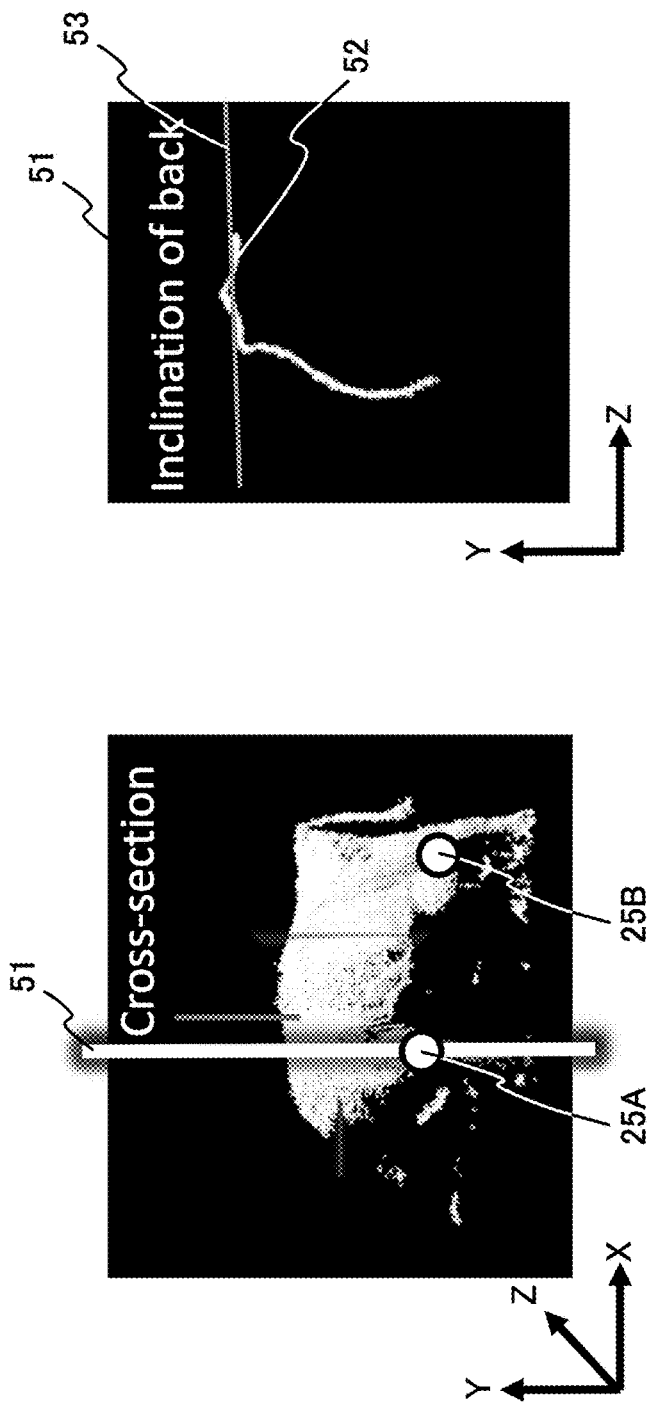
Fig. 6 (a)
Fig. 6 (b)
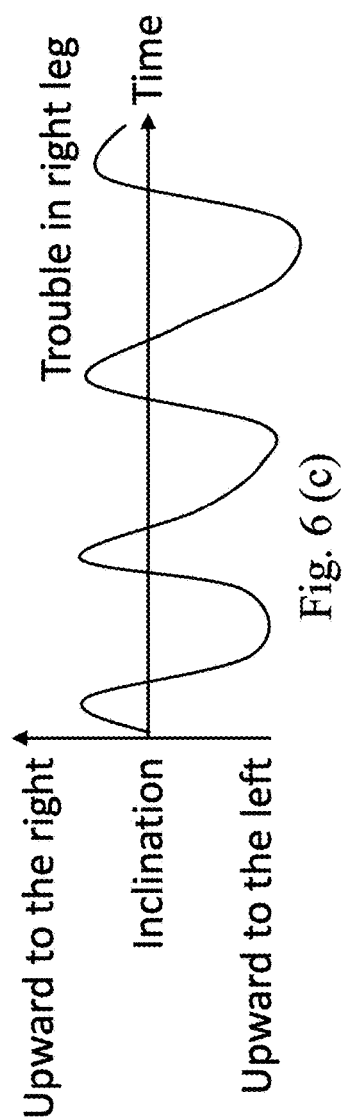
Fig. 6 (c)

| Feature amount (kernel) | Correct answer rate (%) | Correct answer rate with respect to class 1 (%) | Correct answer rate with respect to class 2 (%) |
|---|---|---|---|
| Average depth (RBF) | 92.4 | 100 | 69.0 |
| Average silhouette (RBF) | 99.2 | 100 | 96.9 |
| Average depth (Linear) | 72.8 | 89.3 | 22.5 |
| Average silhouette (Linear) | 71.9 | 93.4 | 6.2 |

Fig. 10

HEALTH CONDITION ESTIMATION DEVICE

TECHNICAL FIELD

The present invention relates to a health condition estimation device which estimates the health condition of a cow.

BACKGROUND ART

Conventionally, for health management of a cow, cow signal scores configured of a body condition score, a rumen fill score, and a locomotion score are used. Although these cow signal scores are quantified by visual confirmation by a veterinarian or a dairyman, problems such as frequency of medical examination and oversight by a dairyman in daily busy work arise, and automation of health management is desired. As such research, research is conducted to determine hoof diseases by attaching a triaxial acceleration sensor to a cow and analyzing a signal from the sensor (see Non Patent Literature 1). However, such a wearable sensor is undesirable because attachment of the sensor by a dairyman takes great manpower costs and is stressful for the cow as well.

Therefore, in recent years, a technique for estimating a locomotion score effective for diagnoses of hoof diseases by using a non-wearable sensor such as a camera has been developed (see Non Patent Literature 2). For example, a technique based on image analysis using an RGB camera (see Non Patent Literature 3 and Patent Literature 1) has been proposed.

CITATION LIST

Patent Literature

Patent Literature 1: JP 2015-173732 A

Non Patent Literature

Non Patent Literature 1: Okada, Kobayashi, Hanada, Hiranuma, Hayashi, Arashi, Chida, Deguchi, Sato, "Detection of hoof diseases in cow using a triaxial accelerometer", Japanese Journal of Large Animal Clinics, Vol. 2, No. 4, pp. 183-188, 2011.
Non Patent Literature 2: A. Schlageter-Tello, E. Bokkers, P. Koerkamp, et al, "Manual and automatic locomotion scoring systems in dairy cows: A review", Preventive veterinary medicine, Vol. 116, No. 1, pp. 12-25, 2014.
Non Patent Literature 3: A. Poursaberi, C. Bahr, A. Pluk, et al, "Real-time automatic lameness detection based on back posture extraction in dairy cattle: Shape analysis of cow with image processing techniques", Computers and Electronics in Agriculture, Vol. 74, No. 1, pp. 110-119, 2010.

SUMMARY OF INVENTION

Technical Problems

However, in the technique disclosed in Non Patent Literature 3, features necessary for score estimation are given manually, and fully automation has not been realized. In addition, in the techniques disclosed in Non Patent Literature 3 and Patent Literature 1, score estimation is performed by processing an image captured by the RGB camera. Therefore, in order to accurately estimate the score, it is necessary to observe a cow from a specific direction. However, making a cow follow human instructions and remain stationary at a specific location is difficult and is also stressful for the cow. In addition, in order to make a cow remain stationary with respect to the camera, special equipment and the like are required and there is a problem in terms of costs.

In addition, in a case where accurate positioning of a cow is impossible, there is also a problem in the accuracy of score estimation.

The present invention has been made in view of such circumstances, and an object of the present invention is to provide a health condition estimation device capable of accurately estimating the health condition of a cow without requiring accurate positioning of the cow.

Solution to Problems

In order to achieve the above object, a health condition estimation device according to an aspect of the present invention is a health condition estimation device which estimates a health condition of a cow, the device including: a three-dimensional coordinates acquisition unit which acquires a group of three-dimensional coordinates representing a three-dimensional shape of a cow extracted from a distance image of the cow; a feature amount extraction unit which extracts a feature amount of the cow, according to the group of three-dimensional coordinates acquired by the three-dimensional coordinates acquisition unit; and a score calculation unit which calculates a score that indicates a health condition of the cow, according to the feature amount extracted by the feature amount extraction unit.

A health condition estimation device according to another aspect of the present invention is a health condition estimation device which estimates a health condition of a cow, the device including: a three-dimensional coordinates acquisition unit which acquires a group of three-dimensional coordinates representing a three-dimensional shape of a cow extracted from a distance image of the cow; and a score calculation unit which calculates a score corresponding to the group of three-dimensional coordinates acquired by the three-dimensional coordinates acquisition unit by associating a standard model of the group of three-dimensional coordinates of the cow classified for each score indicating a health condition of a cow with the group of three-dimensional coordinates acquired by the three-dimensional coordinates acquisition unit.

Note that the present invention can be realized not only as a health condition estimation device including such characteristic processing units but also as a health condition estimation method including as steps processes executed by the characteristic processing units included in the health condition estimation device. In addition, the present invention can also be realized as a program for causing a computer to function as the characteristic processing units included in the health condition estimation device. It goes without saying that such a program can be distributed via a non-transitory computer-readable recording medium such as a CD-ROM (Compact Disc-Read Only Memory) or a communication network such as the Internet. In addition, the present invention can be realized as a semiconductor integrated circuit realizing part or entirety of the health condition estimation device, or can be realized as a health condition estimation system including the health condition estimation device.

Advantageous Effects of Invention

According to the present invention, it is possible to accurately estimate the health condition of a cow without performing accurate positioning of the cow.

BRIEF DESCRIPTION OF DRAWINGS

FIGS. 4 (a) to 4 (d) are diagrams for explaining a process of extracting a feature amount indicating the degree of sinking of a rumen.

FIGS. 6 (a) to 6 (c) are diagrams for explaining a process of extracting a feature amount of a walking state of a cow.

FIG. 10 is a diagram illustrating results of performing classification of locomotion scores into classes using a SVM (Support Vector Machine).

DESCRIPTION OF EMBODIMENTS

Figure 1:
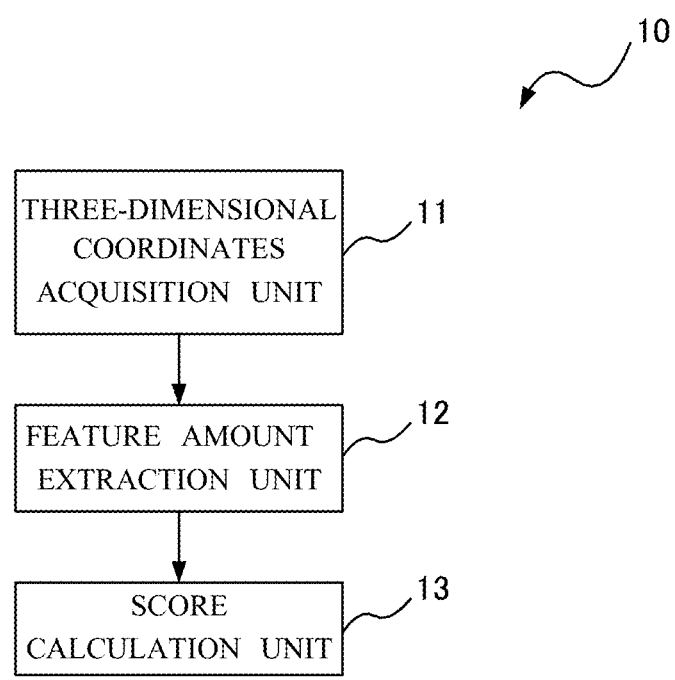
FIG. 1 is a block diagram illustrating a functional configuration of a health condition estimation device according to Embodiment 1 of the present invention.

First, embodiments of the present invention will be listed and explained.

(1) In order to achieve the above object, a health condition estimation device according to an embodiment of the present invention is a health condition estimation device which estimates a health condition of a cow, the device including: a three-dimensional coordinates acquisition unit which acquires a group of three-dimensional coordinates representing a three-dimensional shape of a cow extracted from a distance image of the cow; a feature amount extraction unit which extracts a feature amount of the cow, according to the group of three-dimensional coordinates acquired by the three-dimensional coordinates acquisition unit; and a score calculation unit which calculates a score that indicates a health condition of the cow, according to the feature amount extracted by the feature amount extraction unit.

According to this configuration, a feature amount is extracted from a group of three-dimensional coordinates representing the three-dimensional shape of a cow and a score that indicates the health condition of the cow is calculated according to the feature amount. The group of three-dimensional coordinates can be obtained from the distance image. Therefore, even if the posture of a cow is inclined to some degree with respect to a camera, it is possible to calculate the accurate three-dimensional coordinates of the cow from the distance image. Therefore, it is possible to accurately estimate the health condition of a cow without performing accurate positioning of the cow.

(2) It is preferable: that the feature amount extraction unit extracts a feature amount that indicates a degree of sinking of a rumen of the cow, according a group of three-dimensional coordinates of a rumen area in the group of three-dimensional coordinates acquired by the three-dimensional coordinates acquisition unit, the rumen area being an area on a body surface of the cow proximal to the rumen of the cow; and that the score calculation unit calculates a rumen fill score of the cow, according to the feature amount extracted by the feature amount extraction unit and indicating the degree of sinking of the rumen.

By using a group of three-dimensional coordinates, it is possible to quantify the degree of sinking of the rumen (first stomach of a cow) as a feature amount. Therefore, it is possible to accurately calculate the rumen fill score.

(3) It is more preferable that the feature amount extraction unit extracts a histogram of the curvature in the rumen area as the feature amount indicating the degree of sinking of the rumen, according to the group of three-dimensional coordinates of the rumen area.

In a case where the rumen area does not sink, the curvature of the area becomes relatively small; however, in a case where the rumen area sinks, the curvature becomes relatively great. Therefore, by using the histogram of the curvature as the feature amount indicating the degree of sinking of the rumen, it is possible to accurately calculate the rumen fill score.

(4) In addition, the feature amount extraction unit may extract a distance between the rumen area and a predetermined plane applied to the rumen area as the feature amount indicating the degree of sinking of the rumen, according to the group of three-dimensional coordinates of the rumen area.

In a case where the rumen area does not sink, the distance between the area and the predetermined plane becomes relatively small; however, in a case where the rumen area sinks, the distance becomes relatively large. Therefore, by using the distance as the feature amount indicating the degree of sinking of the rumen, it is possible to accurately calculate the rumen fill score.

(5) In addition, the feature amount extraction unit may extract a volume of a space between a convex hull surrounding the rumen area and the rumen area as the feature amount indicating the degree of sinking of the rumen, according to the group of three-dimensional coordinates of the rumen area.

In a case where the rumen area does not sink, the volume of the space between the convex hull surrounding the rumen area and the rumen area becomes relatively small; however, in a case where the rumen area sinks, the volume becomes relatively large. Therefore, by using the volume as the feature amount indicating the degree of sinking of the rumen, it is possible to accurately calculate the rumen fill score.

(6) It is more preferable that the three-dimensional coordinates acquisition unit acquires a time-series group of three-dimensional coordinates from time-series distance images of the cow, and the feature amount extraction unit extracts a feature amount indicating a degree of sinking of the rumen obtained when the degree of sinking of the rumen is greatest, according to the time-series group of three-dimensional coordinates of the rumen area.

According to this configuration, since the time-series group of three-dimensional coordinates is used, it is possible to extract the feature amount obtained when the degree of sinking of the rumen is greatest. It is considered that veterinarians and dairymen determine the rumen fill score according to the shape of the rumen area obtained when the degree of sinking of the rumen is greatest. Therefore, since it is possible to calculate the rumen fill score under conditions identical to those for veterinarians and dairymen, it is possible to calculate the rumen fill score more accurately.

(7) It is preferable that the feature amount extraction unit detects a back line of the cow, according to the group of three-dimensional coordinates acquired by the three-dimensional coordinates acquisition unit, and extracts as a feature amount of the back line a parameter of a predetermined curve obtained by fitting the predetermined curve to the back line which is detected, and that the score calculation unit calculates a locomotion score of the cow according to the feature amount of the back line extracted by the feature amount extraction unit.

The back line of a cow has a curved shape. Therefore, the parameter of a curve obtained by fitting the curve to the back line can be used as the feature amount of the back line. Therefore, it is possible to accurately calculate the locomotion score according to the feature amount of the back line.

(8) In addition, the feature amount extraction unit may detect a back line of the cow, according to the group of three-dimensional coordinates acquired by the three-dimensional coordinates acquisition unit, and may extract as a feature amount of the back line a shift amount of the back line which is detected from a predetermined line, and the score calculation unit may calculate a locomotion score of the cow according to the feature amount of the back line extracted by the feature amount extraction unit.

For example, assuming that the predetermined line is a straight line, in the case of a cow whose backbone is curved, the back line is also curved. Therefore, the shift amount from the predetermined line becomes relatively great. In contrast, in the case of a cow whose backbone is not curved, the back line is not curved so much. Therefore, the shift amount becomes relatively small. Therefore, it is possible to accurately calculate the locomotion score by using the shift amount as the feature amount of the back line.

(9) It preferable that the three-dimensional coordinates acquisition unit acquires a time-series group of three-dimensional coordinates from time-series distance images of the cow, and the feature amount extraction unit extracts the feature amount of the cow, according to the time-series group of three-dimensional coordinates.

According to this configuration, the time-series group of three-dimensional coordinates represents three-dimensional movement of the cow. Therefore, the feature amount of the cow based on the time-series group of three-dimensional coordinates is a value characterizing movement of the cow. Therefore, it is possible to calculate the score of the cow according to movement of the cow. Therefore, it is possible to accurately estimate the health condition regarding movement of the cow.

(10) It is more preferable that the feature amount extraction unit extracts a feature amount of a walking state of the cow according to the time-series group of three-dimensional coordinates, and that the score calculation unit calculates a locomotion score of the cow according to the feature amount of the walking state of the cow extracted by the feature amount extraction unit.

According to this configuration, it is possible to extract the feature amount indicating the walking state of the cow by using the time-series group of three-dimensional coordinates. Therefore, it is possible to accurately calculate the locomotion score of the cow according to the above feature amount.

(11) In addition, the feature amount extraction unit may extract, as the feature amount of the walking state of the cow, a value indicating variation in a degree of inclination in a right/left direction during walking of the cow, according to the time-series group of three-dimensional coordinates.

According to this configuration, for example, the manner of walking inclined to the left such that the left shoulder is located lower than the right shoulder can be represented as a feature amount. Therefore, it is possible to accurately calculate the locomotion score of the cow according to the above feature amount.

(12) In addition, the feature amount extraction unit may extract, as the feature amount of the walking state of the cow, a value indicating movement of a leg during walking of the cow, according to the time-series group of three-dimensional coordinates.

According to this configuration, for example, the step length of a cow, the amount of protrusion of a leg from the width of the trunk, or the like can be quantified and expressed as a feature amount. Therefore, it is possible to accurately calculate the locomotion score of the cow according to the above feature amount.

(13) In addition, the feature amount extraction unit may extract, as the feature amount of the walking state of the cow, a gait feature amount of the cow, according to the time-series group of three-dimensional coordinates.

According to this configuration, it is possible to express a walking manner of a cow as a gait feature amount. Therefore, it is possible to accurately calculate the locomotion score of a cow according to such a gait feature amount.

(14) It is preferable that the feature amount extraction unit may extract a feature amount indicating a width of a body or a position of a backbone of the cow, according to the group of three-dimensional coordinates acquired by the three-dimensional coordinates acquisition unit, and the score calculation unit may calculate a body condition score of the cow according to the feature amount indicating the width of the body or the position of the backbone of the cow.

According to this configuration, for example, the maximum width of the body, the height of the backbone along the body, or the like of a cow can be quantified and expressed as a feature amount. Therefore, it is possible to accurately calculate the body condition score of a cow according to the above feature amount.

(15) A health condition estimation device according to another embodiment of the present invention is a health condition estimation device which estimates a health condition of a cow, the device including: a three-dimensional coordinates acquisition unit which acquires a group of three-dimensional coordinates representing a three-dimensional shape of a cow extracted from a distance image of the cow; and a score calculation unit which calculates a score of the cow corresponding to the group of three-dimensional coordinates acquired by the three-dimensional coordinates acquisition unit by associating a standard model of a group of three-dimensional coordinates of the cow classified for each score indicating a health condition of a cow with the group of three-dimensional coordinates acquired by the three-dimensional coordinates acquisition unit.

The group of three-dimensional coordinates closest to the group of three-dimensional coordinates acquired by the three-dimensional coordinates acquisition unit can be selected from among standard models of groups of three-dimensional coordinates of the cow classified in advance for each score. In addition, the score corresponding to the selected standard model can be used as the score of the cow. The group of three-dimensional coordinates can be obtained from the distance image. Therefore, even if the posture of a cow is inclined to some degree with respect to a camera, it is possible to calculate the accurate three-dimensional coordinates of the cow from the distance image. Therefore, it is possible to accurately estimate the health condition of a cow without performing accurate positioning of the cow.

DETAILED DESCRIPTION OF EMBODIMENTS

Hereinafter, embodiments of the present invention will be described in detail with reference to the drawings. Note that each of the embodiments described below describes one preferable specific example of the present invention. Numerical values, shapes, materials, constituent elements, arrangement positions and connection modes of the constituent elements, steps, order of steps, and the like described in the following embodiments are examples only and are not intended to limit the present invention. The present invention is specified by the claims. Therefore, a description will be given assuming that among the constituent elements in the following embodiments, constituent elements not described in an independent claim representing the most generic concept of the present invention are not necessarily required to solve the problem of the present invention, but constitute a preferable mode.

Embodiment 1

Hereinafter, a health condition estimation device which estimates the health condition of a cow such as a dairy cow will be described. That is, the health condition estimation device will be described which calculates as a health condition of a cow, cow signal scores configured of a body condition score, a rumen fill score, and a locomotion score.

The body condition score is a score indicating the degree of accumulation of cow's body fat. The rumen fill score is a score indicating the degree of fullness of a rumen (first stomach of a cow) with dry food. The locomotion score is a score indicating the degree of lameness of a cow.

[Configuration of Health Condition Estimation Device]

FIG. 1 is a block diagram illustrating a functional configuration of a health condition estimation device according to Embodiment 1 of the present invention.

A health condition estimation device 10 is a device which estimates the health condition of a cow and includes a three-dimensional coordinates acquisition unit 11, a feature amount extraction unit 12, and a score calculation unit 13.

The three-dimensional coordinates acquisition unit 11 acquires a group of three-dimensional coordinates representing the three-dimensional shape of a cow extracted from a distance image of the cow. For example, it is assumed that a distance image sensor is attached to a location near a milking machine in a cowshed, such as a robot milking machine or a milking parlor, and at a location where the distance image sensor can image an upper left side of a cow. The distance image sensor is a sensor that irradiates a target with infrared light and measures the distance to the target according to the reflection time. The three-dimensional coordinates acquisition unit 11 acquires a group of three-dimensional coordinates extracted from the distance image imaged by the distance image sensor. Conversion from the distance image to the three-dimensional coordinates may be performed by the distance image sensor or by the health condition estimation device 10. Note that the three-dimensional coordinates acquisition unit 11 can obtain the group of three-dimensional coordinates of a cow by performing background subtraction of the group of three-dimensional coordinates.

The feature amount extraction unit 12 extracts the feature amount of the cow according to the group of three-dimensional coordinates acquired by the three-dimensional coordinates acquisition unit 11. That is, the feature amount extraction unit 12 extracts one of the following first to tenth feature amounts. Here, each of the first to third feature amounts is a feature amount indicating the degree of sinking of the rumen of a cow and used for calculating the rumen fill score. Each of the fourth and fifth feature amounts is a feature amount of the back line of a cow and is used for calculating the locomotion score. Each of the sixth to eighth feature amounts is a feature amount indicating the walking state of a cow and used for calculating the locomotion score. Each of the ninth and tenth feature amounts is a feature amount indicating the body shape of a cow and used for calculating the body condition score.

(First Feature Amount) Local Curvature Histogram of Rumen Area

The feature amount extraction unit 12 extracts a feature amount that indicates a degree of sinking of the rumen of a cow, according a group of three-dimensional coordinates in a rumen area, in the group of three-dimensional coordinates acquired by the three-dimensional coordinates acquisition unit 11, the rumen area being an area on a body surface of the cow proximal to the rumen of the cow.

Figure 2:
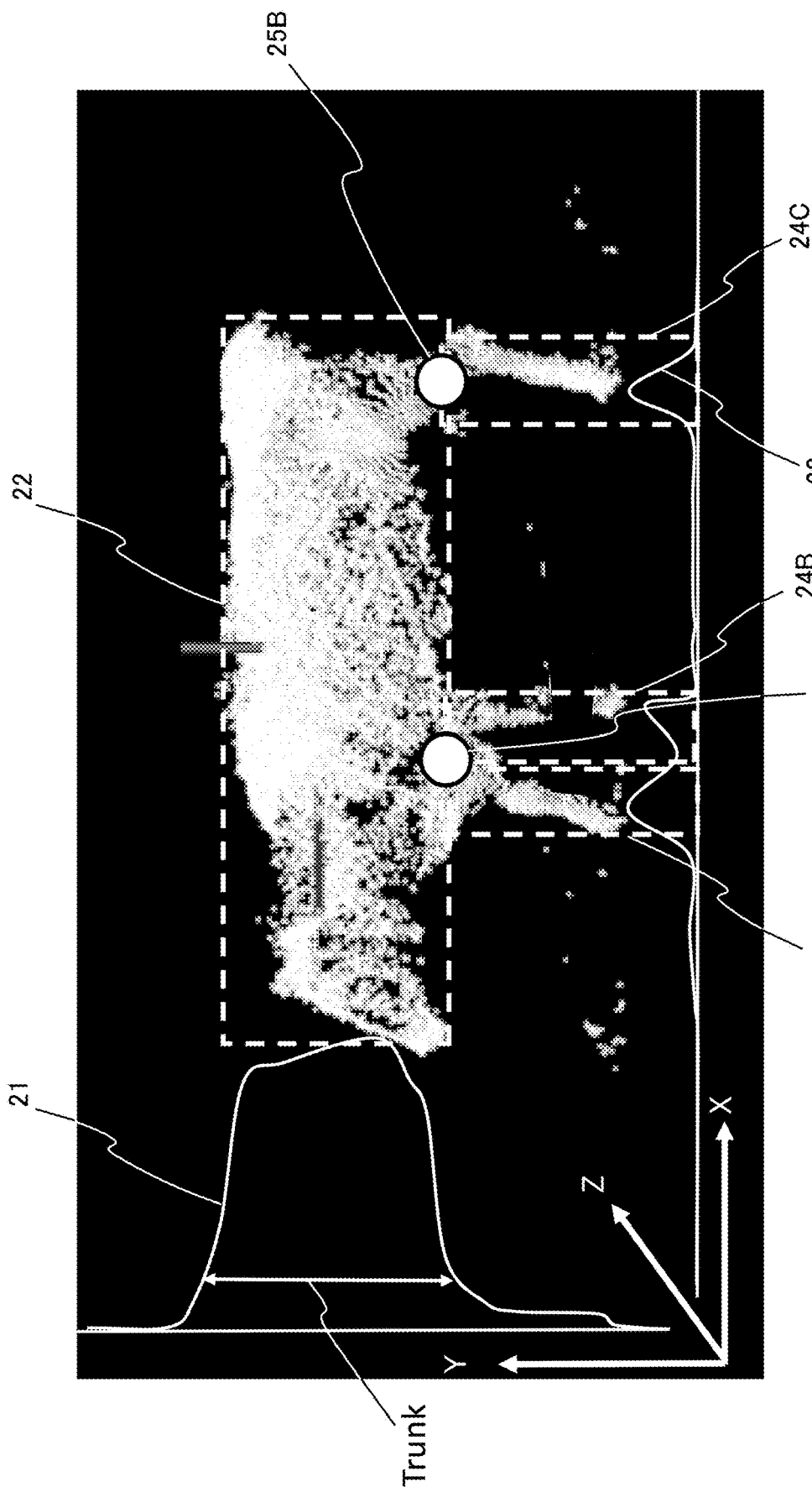
FIG. 2 is a view for explaining a method of specifying the trunk position and groin positions of a cow.

First, the feature amount extraction unit 12 specifies the trunk position and groin positions of a cow from the group of three-dimensional coordinates acquired by the three-dimensional coordinates acquisition unit 11. FIG. 2 is a view for explaining a method of specifying the trunk position and groin positions of a cow. In FIG. 2, a white point indicates three-dimensional coordinates of the cow. Note that it is assumed that coordinate transformation is performed in advance such that the front-rear direction of the cow is the X axis, the vertical direction is the Y axis, and the direction orthogonal to the X axis and the Y axis is the Z axis. For example, the main axis direction of the group of three-dimensional coordinates may be set as the X axis. This coordinate transformation may be performed by the feature amount extraction unit 12.

(1) The feature amount extraction unit 12 projects the group of three-dimensional coordinates on a two-dimensional projection plane (YZ plane) vertical to the ground, and further projects them on the Y axis. The feature amount extraction unit 12 counts the number of projection points on the projection plane for each height from the ground (along the Y axis) (curve 21). In a trunk part, the number of projection points increases. Therefore, in a case where the total number of points constituting the shape of the cow is N and the number of projection points of at a height is p, it is assumed that the trunk is positioned at the heights satisfying $$p/N > \theta \qquad \text{(Expression 1),}$$

wherein, θ is a threshold and θ is determined depending on the proportion of the trunk to the surface area of the cow and resolution of the height of the projection plane. The feature amount extraction unit 12 sets a set of point groups included at the heights where the trunk is present as a point group of the trunk and sets a rectangular parallelepiped including the point group as a trunk area 22.

(2) Next, the feature amount extraction unit 12 projects a three-dimensional point groups located lower than the height determined to be the trunk area 22 on a plane (XZ plane) equal to the ground surface (curve 23). The feature amount extraction unit 12 performs a threshold process similarly to (1), and specifies areas 24A to 24C where legs exist. The feature amount extraction unit 12 sets the areas 24A and 24B in the front half of the trunk as fore-leg areas and the area 24C in the rear half as a hind-leg area.

(3) Assuming that $Y_{bottom}$ represents the height of the lower end of the trunk area 22, and $(X_g, 0, Z_g)$ represents barycentric coordinates of the three-dimensional point group included in the fore-leg area on the XZ projection plane, the feature amount extraction unit 12 calculates the three-dimensional coordinates of a groin 25A of the fore leg as follows.

$$(X_g, Y_{bottom}, Z_g)$$

The feature amount extraction unit 12 similarly obtains the coordinates of a groin 25B of the hind leg.

Figure 3:
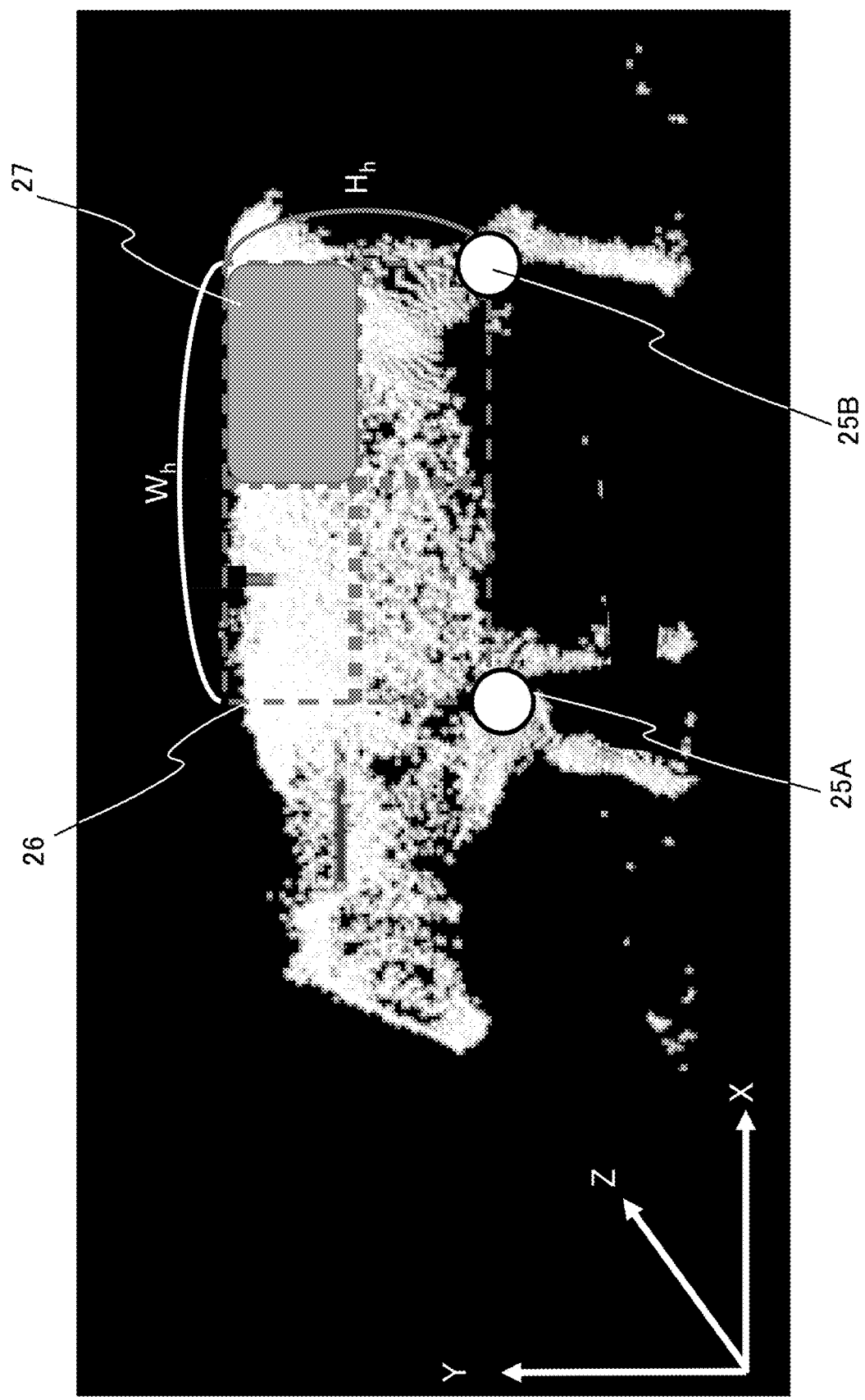
FIG. 3 is a view for explaining a method of extracting a rumen area.

(4) The feature amount extraction unit 12 extracts a three-dimensional point group (rumen area) around the rumen from the relative positional relationship between the detected trunk area 22 and the detected groins 25A and 25B. FIG. 3 is a view for explaining a method of extracting the rumen area.

The feature amount extraction unit 12 extracts an area 26 between the groins 25A and 25B of the fore and hind legs, in the trunk area 22.

Assuming that $W_h$ represents the X coordinate of the midpoint of the groin of the leg, $H_h$ represents the Y coordinate of the center of the trunk height, and $D_h$ represents the Z coordinate of the center of depth of the trunk, the feature amount extraction unit 12 extracts points p that satisfy the condition $x_p > W_h \cap y_p > H_h \cap z_p < D_h$ among the three-dimensional points $p=(x_p, y_p, z_p)$ included in the area 26 as points included in the rumen area 27.

(5) For each point included in the rumen area 27, the feature amount extraction unit 12 calculates the curvature from the positional relationship with a neighborhood point group. For example, the curvature of each point 32 is calculated as illustrated in FIG. 4 (a). The feature amount extraction unit 12 creates a histogram of the calculated curvatures. For example, as illustrated in FIG. 4 (b), a histogram is created in which the horizontal axis indicates a curvature and the vertical axis indicates frequency.

The feature amount extraction unit 12 extracts the histogram of the curvature of each point 32 included in the rumen area 27 calculated in this manner as a feature amount indicating the degree of sinking of the rumen.

(Second Feature Amount) Distance from Plane of Rumen Area

In addition, the feature amount extraction unit 12 may extract the following feature amount as a feature amount indicating the degree of sinking of the rumen.

That is, the feature amount extraction unit 12 applies one plane to the rumen area 27 by using a plane fitting method. For example, a plane for which the sum of squares of distances to the respective points included in the rumen area 27 is minimal may be fitted to the rumen area 27 using a least squares method.

With reference to FIG. 4 (c), the feature amount extraction unit 12 calculates a binary feature indicating on which of the front surface and the back surface of the plane 31 fitted to the rumen area 27 each point 32 included in the rumen area 27 is located or a signed distance from the plane 31 to each point. For example, the feature amount extraction unit 12 may extract for each point 32 a binary feature indicating 1 in a case where the point 32 is on the front surface of the plane 31, and a binary feature indicating 0 in a case where the point 32 is on the back surface. Note that the value indicated by the binary feature is not limited to 1 and 0. In addition, the feature amount extraction unit 12 may calculate the signed distance by setting the distance to the plane 31 to be positive in a case where the point 32 is located on the front surface of the plane 31 and setting the distance to the plane to be negative in a case where the point 32 is located on the back surface of the plane 31. Note that positive and negative of the signed distance may be reversed.

The feature amount extraction unit 12 extracts, as a feature amount indicating the degree of sinking of the rumen, the histogram of the extracted binary features or the signed distances, or two-dimensional distribution of the binary features or the signed distances on the plane 31.

(Third Feature Amount) Volume Feature Amount of Rumen Area

In addition, the feature amount extraction unit 12 may extract the following feature amount as a feature amount indicating the degree of sinking of the rumen.

That is, as illustrated in FIG. 4 (d), the feature amount extraction unit 12 generates a convex hull 33 surrounding the rumen area 27. The convex hull 33 is formed as a plane or part of an ellipsoid. The convex hull 33 can be calculated using a known three-dimensional convex hull calculation method.

The feature amount extraction unit 12 extracts the volume of a space 34 between the group of three-dimensional coordinates included in the rumen area 27 and the convex hull 33 as a feature amount indicating the degree of sinking of the rumen.

Note that it is preferable that the first to third feature amounts are extracted in a state where the rumen sinks most. Therefore, the feature amount extraction unit 12 extracts a feature amount indicating the degree of sinking of the rumen obtained when the degree of sinking of the rumen is greatest, according to a time-series group of three-dimensional coordinates of the rumen area.

For example, the time when the sum of absolute values of distances between the respective points 32 included in the rumen area 27 illustrated in FIG. 4 (c) and the plane 31 is greatest may be defined as the time when the degree of sinking of the rumen is greatest. In addition, the time when the volume of the space 34 illustrated in FIG. 4 (d) is greatest may be defined as the time when the degree of sinking of the rumen is greatest. It is considered that veterinarians and dairymen determine the rumen fill score according to the shape of the rumen area obtained when the degree of sinking of the rumen is greatest. Therefore, since it is possible to calculate the rumen fill score under conditions identical to those for veterinarians and dairymen, it is possible to calculate the rumen fill score more accurately.

(Fourth Feature Amount) Curve Parameter of Back Line

The feature amount extraction unit 12 extracts the feature amount of a back line of a cow according to the group of three-dimensional coordinates acquired by the three-dimensional coordinates acquisition unit 11.

Figure 5:
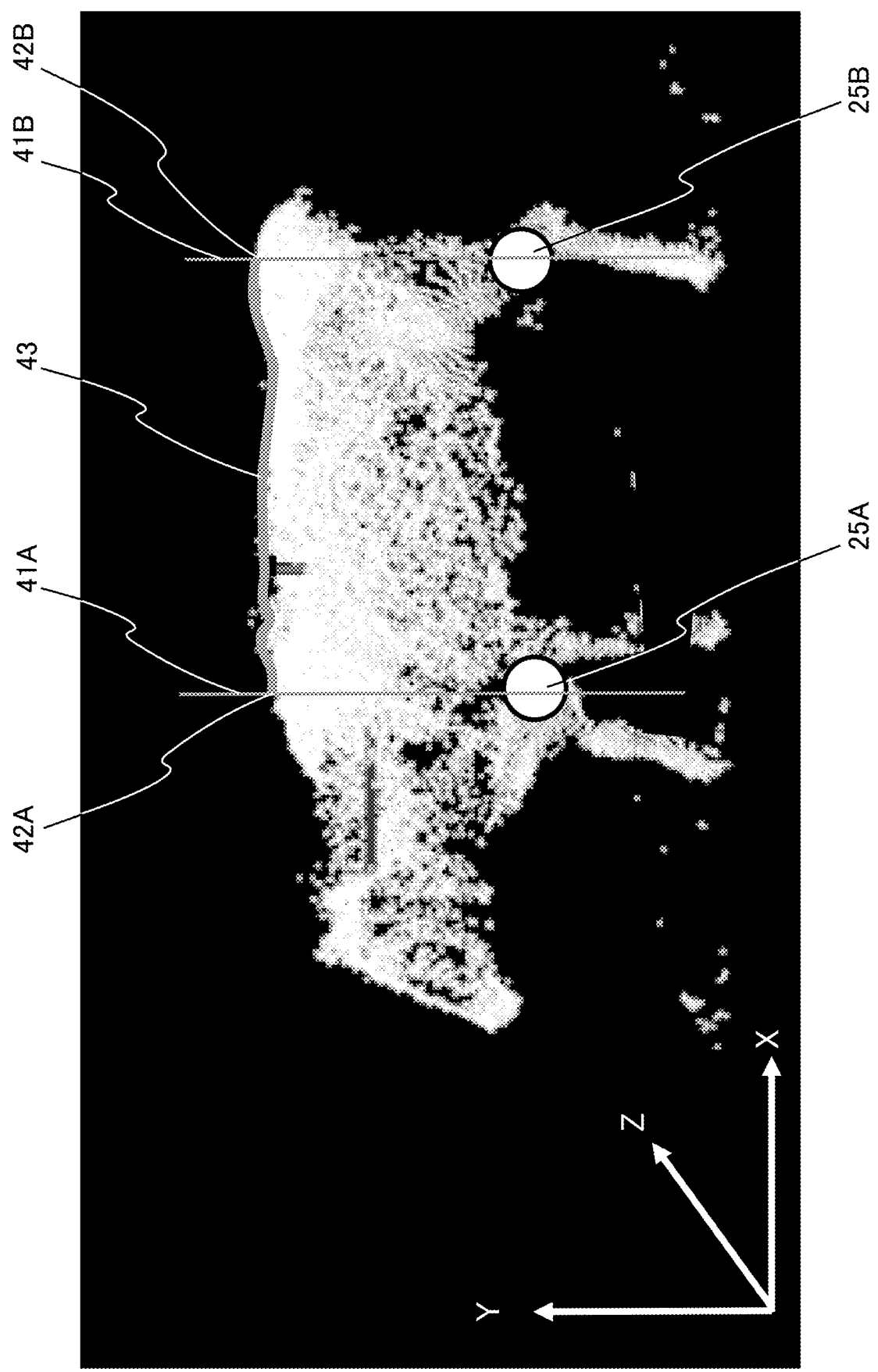
FIG. 5 is a view for explaining a method of extracting the back line of a cow.

FIG. 5 is a view for explaining a method of extracting the back line of a cow.

(1) The feature amount extraction unit 12 projects all the groups of three-dimensional coordinates of a cow on the XY plane.

(2) The feature amount extraction unit 12 sets, as a start point 42A and an end point 42B of the back line, points which pass through points obtained by projecting the three-dimensional coordinates of the groins 25A and 25B of the fore and the hind legs on the XY plane, and which are the highest points (points with the Y coordinates greatest) on straight lines 41A and 41B parallel to the Y axis, respectively.

(3) The feature amount extraction unit 12 determines a back line 43 connecting the start point 42A and the end point 42B by one of the following methods.

That is, the feature amount extraction unit 12 sets the locus of the highest points (points with the greatest Y coordinates) along the X axis as the back line 43. Here, when the highest points are detected, a technique of removing observation noise of a point group may also be used.

Alternatively, the feature amount extraction unit 12 may set a straight line which is located sufficiently higher than the highest points and which is parallel to the straight line connecting the start point 42A and the end point 42B, may fit the back line 43 to the group of three-dimensional coordinates by using an active contour method with the set straight line as an initial value.

(4) The feature amount extraction unit 12 extracts the parameter of a predetermined curve obtained by fitting the predetermined curve to the detected back line 43 as the feature amount of the back line 43.

For example, the feature amount extraction unit 12 fits a quadratic curve, a circle, an ellipse, or a quartic curve to the back line 43, and extracts the parameter representing the above curve as the feature amount of the back line 43.

In addition, the feature amount extraction unit 12 may fit a local quadratic curve to the back line 43, may calculate a histogram of the local curvature, and may extract the histogram as the feature amount of the back line 43.

(Fifth Feature Amount) Shift of Back Line from Straight Line

The feature amount extraction unit 12 may extract the shift amount of the detected back line 43 from a predetermined line as the feature amount of the back line. For example, a value obtained by normalizing the sum of the distances between the straight line connecting the start point 42A and the end point 42B of the back line 43 and the respective points on the back line 43 by the length of the straight line may be extracted as the feature amount of the back line 43. For example, the respective points on the back line 43 may be selected at equal intervals. Further, in lieu of each point on the back line 43, a point on the curve fitted to the back line 43 may be used.

In addition, the feature amount extraction unit 12 may extract the ratio of the length of the back line 43 to the length of the straight line connecting the start point 42A and the end point 42B of the back line 43 as the feature amount of the back line 43.

(Sixth Feature Amount) Time Change of Both Shoulder Heights

The feature amount extraction unit 12 may acquire a time-series group of three-dimensional coordinates from time-series distance images of a cow, and may extract a feature amount of the cow, according to the time-series group of three-dimensional coordinates. In the sixth to eighth feature amounts, examples of extracting a feature amount of the walking state of a cow as the feature amount of the cow will be described.

Before extracting the feature amount, the feature amount extraction unit 12 performs alignment of the groups of three-dimensional coordinates so that the positions of the whole body or the trunk of the cow are associated with each other between the time-series groups of three-dimensional coordinates. This alignment of the groups of three-dimensional coordinates is performed by using, for example, the ICP (Iterative Closest Point) method or the Coherent Point Drift method.

Next, the feature amount extraction unit 12 extracts, as the feature amount of the walking state of the cow, a value indicating variation in the degree of inclination in a right/left direction during walking of the cow, according to the time-series group of three-dimensional coordinates. In other words, one or both of the following techniques 1 and 2 are extracted as the feature amounts of the walking state of the cow.

(Technique 1) Technique of Using Non-Uniformity of Change in Heights of Both Shoulders With reference to FIG. 6 (*a*), the feature amount extraction unit 12 cuts the group of three-dimensional coordinates by a plane 51 passing through the groin 25A of the fore leg and parallel to the YZ plane, and thus extracts the group of three-dimensional coordinates included in the plane 51. Similarly, with respect to the groin 25B of the hind leg, the group of three-dimensional coordinates included in the plane 51 is extracted.

With reference to FIG. 6 (*b*), with respect to each plane 51, the feature amount extraction unit 12 applies a straight line 53 to the group of three-dimensional coordinates belonging to the back in the group of three-dimensional coordinates belonging to the plane 51, and calculates inclination of the straight line 53. The inclination is calculated over a predetermined number of walking cycles or a predetermined time. As a result, a graph in which the horizontal axis indicates time and the vertical axis indicates inclination as illustrated in FIG. 6 (*c*) is obtained. Note that the group of three-dimensional coordinates belonging to the back may be, for example, a group of coordinates within a predetermined distance in the Y-axis direction from the coordinates with the greatest Y-coordinate in the group of three-dimensional coordinates belonging to the plane 51. In addition, for example, the straight line 53 may be a straight line for which the sum of squares of the distances to the group of three-dimensional coordinates belonging to the back is minimal.

The feature amount extraction unit 12 calculates a variation scale of walking according to the following expression 2 and sets the calculated variation scale as the feature amount of the walking state of the cow.

$$\text{Variation scale of walking} = |\text{Time when inclination is positive} - \text{Half of walking}| \quad \text{(Expression 2)}$$

(Technique 2) Technique Using Fourier Transform

Similarly to technique 1, for each of the plane 51 passing through the groin 25A of the fore leg and the plane 51 passing through the groin 25B of the hind leg, the feature amount extraction unit 12 frequency-converts (for example, performs Fourier transformation on) the time-series (more than or equal to one cycle of) group of three-dimensional coordinates belonging to the back in the group of three-dimensional coordinates belonging to each plane 51, to obtain the frequency of vertical movement of the group of three-dimensional coordinates.

Assuming that the i-fold frequency obtained based on frequency conversion is $f_i$, the feature amount extraction unit 12 extracts the feature amount expressed by the following expression 3 or expression 4. Expression 3 represents magnitude of the change in vertical movement, and it is considered that the larger the value of expression 3 is, the more serious trouble in the hoof exists. Expression 4 represents whether the change in vertical movement is close to a sin wave, and the more uneven the way of walking is, the larger the value of expression 4 is.

[Mathematical Expression 1]

$$\sum_{i=1}^{n} f_i \quad \text{(Expression 3)}$$

$$\frac{\sum_{i=1}^{n} f_i}{f_1} \quad \text{(Expression 4)}$$

(Seventh Feature Amount) Movement of Leg

The feature amount extraction unit 12 extracts, as the feature amount of the walking state of the cow, a value indicating movement of the legs during walking of the cow, according to the time-series group of three-dimensional coordinates.

That is, the feature amount extraction unit 12 creates a sliced cross-section parallel to the ground surface (XZ plane) at the height of the midpoint between the ground surface (XZ plane) and the lower end of the trunk area 22, and obtains the position of each leg from the group of three-dimensional coordinates included in the cross-section. For example, clustering of the group of three-dimensional coordinates is performed within the cross-section, and the position of the area having a predetermined size or more may be set as the position of each leg.

The feature amount extraction unit 12 obtains the positions of the respective legs over several walking cycles and calculates the following feature amount of the step length or leg opening from the locus of the legs.

That is, the feature amount extraction unit 12 calculates as the feature amount of the step length, the value obtained by normalizing the shortest distance between the fore leg and the hind leg during walking by the distance between the groins 25A and 25B of the fore leg and the hind leg. Note in a case where the step lengths of the respective four limbs can be calculated, the average of the step lengths may be calculated.

In addition, the feature amount extraction unit 12 calculates how far each leg protrudes outside during walking, with respect to the maximum width in the Z axis direction of the trunk area 22. That is, the feature amount extraction unit 12 may calculate the variance of the distance from the side surface of the trunk area 22 to the leg which protrudes most or of the distance from the side surface of the trunk area 22 to each leg, and may set the calculated value as the feature amount of leg opening.

(Eighth Feature Amount) Gait Feature

The feature amount extraction unit 12 calculates the gait feature amount of a dairy cow, the gait feature amount being used for human gait identification, and sets the gait feature amount as the feature amount of walking state of the cow. This technique can be applied not only to a specific part but to the whole body or each part. Typical examples of gait features are as indicated in the following a to d; however, various other gait features can be used.

a: Two-dimensional silhouette feature and gait feature based on frequency transformation performed thereon (For example, Gait Energy Image (Non Patent Literature 4))

b: Three-dimensional silhouette feature and gait feature based on frequency transformation performed thereon (For example, Depth-based Feature (Non Patent Literature 5))

c: Gait feature without using silhouette (for example, Spatio-Temporal HOG feature using local feature amount histogram (Non Patent Literature 6))

d: Method of calculating the above gait feature not for the whole body but for each part (for example, Non Patent Literature 7)

Non Patent Literature 4: "Individual recognition using gait energy image.", J. Han, B. Bhanu, IEEE Transactions on Pattern Analysis and Machine Intelligence, 28 (2), pp. 316-322, 2006.

Non Patent Literature 5: "Depth-based gait feature representation.", H. Nakajima, I. Mitsugami, Y. Yagi, IPSJ Trans. on Computer Vision and Applications, vol. 5, pp. 94-98, 2013.

Non Patent Literature 6: "Person re-identification using view-dependent score-level fusion of gait and color features.", R. Kawai, Y. Makihara, C. Hua, H. Iwama, Y. Yagi, Proc. 21st International Conference on Pattern Recognition (ICPR), pp. 2694-2697, 2012.

Non Patent Literature 7: "Clothing-invariant gait identification using part-based clothing categorization and adaptive weight control.", M. Hossain, Y. Makihara, J. Wang, Y. Yagi, Pattern Recognition, 43(6) pp. 2281-2291, 2010.

Note that the feature amount extraction unit 12 may use a gait (walking manner) fluctuation feature as a gait feature. In the case of a dairy cow with a gait disturbance, it is considered that there may be variation in the way of dragging a leg or in the degree of progress of the walking posture between cycles. Therefore, the feature amount extraction unit 12 calculates a gait fluctuation feature between cycles as indicated in the following e and f. This technique can be applied not only to a specific part but to the whole body or each part.

e: Variation in the progressing speed of the posture (phase) of gait between cycles is used as temporal fluctuation in the gait.

f: The average of differences in silhouette between cycles is used as spatial fluctuation in the gait.

(Ninth Feature Amount) Feature Amount of Width of Body

The feature amount extraction unit 12 extracts the feature amount indicating the width of the body of a cow according to the group of three-dimensional coordinates acquired by the three-dimensional coordinates acquisition unit 11.

Figure 7:
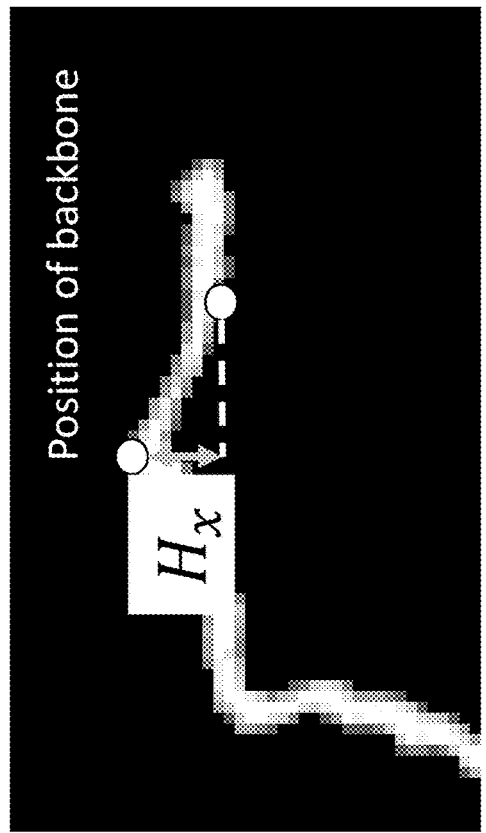
FIGS. 7 (a) and 7 (b) are diagrams for explaining a process of extracting a feature amount of a width of a body and a feature amount of the position of a backbone.
Figure 7:
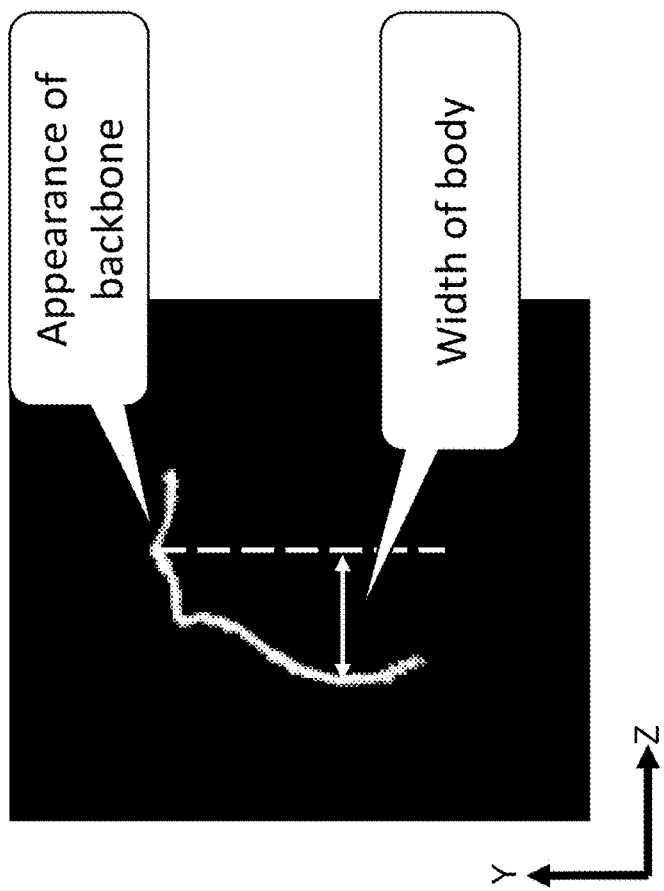

Similarly to FIG. 6 (b), FIG. 7 (a) is a diagram illustrating a group of three-dimensional coordinates belonging to the plane 51. As illustrated in FIG. 7 (a), the distance in the Z axis direction between the three-dimensional coordinates with the greatest Y-coordinate and the three-dimensional coordinates with the smallest Z-coordinate is extracted as the width of the body.

In addition, the feature amount extraction unit 12 may also extract, as the width of the body, the distance in the Z axis direction between the three-dimensional coordinates with the greatest Y-coordinate and the three-dimensional coordinates with the smallest Z coordinate when the cow is viewed from behind. At this time, a process is performed by excluding the three-dimensional coordinates of the neck and the head.

As a result, compared to a case where imaging from right above or right behind by a RGB camera is conventionally necessary, shape measurement by using the distance image sensor enables a similar feature to be calculated by imaging from obliquely above, or the like.

(Tenth Feature Amount) Feature Amount of Position of Backbone

The feature amount extraction unit 12 extracts the feature amount indicating the position of the backbone of a cow according to the group of three-dimensional coordinates acquired by the three-dimensional coordinates acquisition unit 11.

That is, the feature amount extraction unit 12 sets a plurality of planes parallel to the YZ plane at predetermined intervals along the straight line connecting the start point 42A and the end point 42B of the back line illustrated in FIG. 5. Each plane is referred to as a slice. For example, as illustrated in FIG. 7 (*a*), in each slice, a group of three-dimensional coordinates is extracted. With reference to FIG. 7 (*b*), the feature amount extraction unit 12 calculates, for each slice, a difference $H_x$ in height between the highest point (point with the greatest Y-coordinate) of the group of three-dimensional coordinates included in the slice and the point separated by a distance L to the left or right from the highest point. The feature amount extraction unit 12 obtains a feature amount indicating the position of the backbone of a cow by using any one of the following methods a to c.

a: Technique of Using Average

The feature amount extraction unit 12 averages differences in height over the entire back line. That is, assuming that the number of slices is Ns, the feature amount extraction unit 12 calculates a scale $H_b$ according to the following expression 5, and sets the scale $H_b$ as a feature amount indicating the position of the backbone of a cow.

[Mathematical Expression 2]

$$H_B = \frac{1}{N_S} \sum_x H_x \quad \text{(Expression 5)}$$

b: Technique of Using Histogram

The feature amount extraction unit 12 creates a histogram in which the horizontal axis indicates $H_x$ and the vertical axis indicates frequency, and the histogram is set as a feature amount indicating the position of the backbone position of a cow.

c: Technique of Using Change as Feature Amount

The feature amount extraction unit 12 sets the locus of the change of $H_x$ due to movement of the slice along the X axis as the feature amount.

With reference again to FIG. 1, the score calculation unit 13 calculates a rumen fill score, a locomotion score, or a body condition score, according to any one of the first to tenth feature amounts calculated by the feature amount extraction unit 12.

The score calculation unit 13 calculates a score for each feature amount according to a regression model obtained by regression analysis in which each feature amount 60 is set as a predictor variable and the score is set as a criterion variable.

Note that in a case where the feature amount is expressed in a fixed-length dimension, a regression analysis between the score and the feature amount as a predictor variable is performed. Especially, feature extraction from a cow which moves unsteadily includes an outlier and an error. Therefore, by using support vector regression taking into consideration existence of an outlier and Gaussian process regression capable of obtaining an estimated error in addition to an estimated value of the score, it is possible to perform robust score estimation.

In addition, in a case where the feature amount is a time-series signal which does not have a fixed-length dimension, resampling of a feature amount with a fixed-length dimension is performed by using a technique such as self-dynamic time warping and then regression analysis similar to the above is performed. Alternatively, score estimation is performed by using support vector regression, Gaussian process regression, or the like extended to nonlinear regression by assuming that the collation degree based on dynamic time warping applied to a learning set of scores and time-series signal is a kernel function value.

For example, the score calculation unit 13 calculates a score for each feature amount according to a linear regression model obtained in advance by learning.

Figure 8:
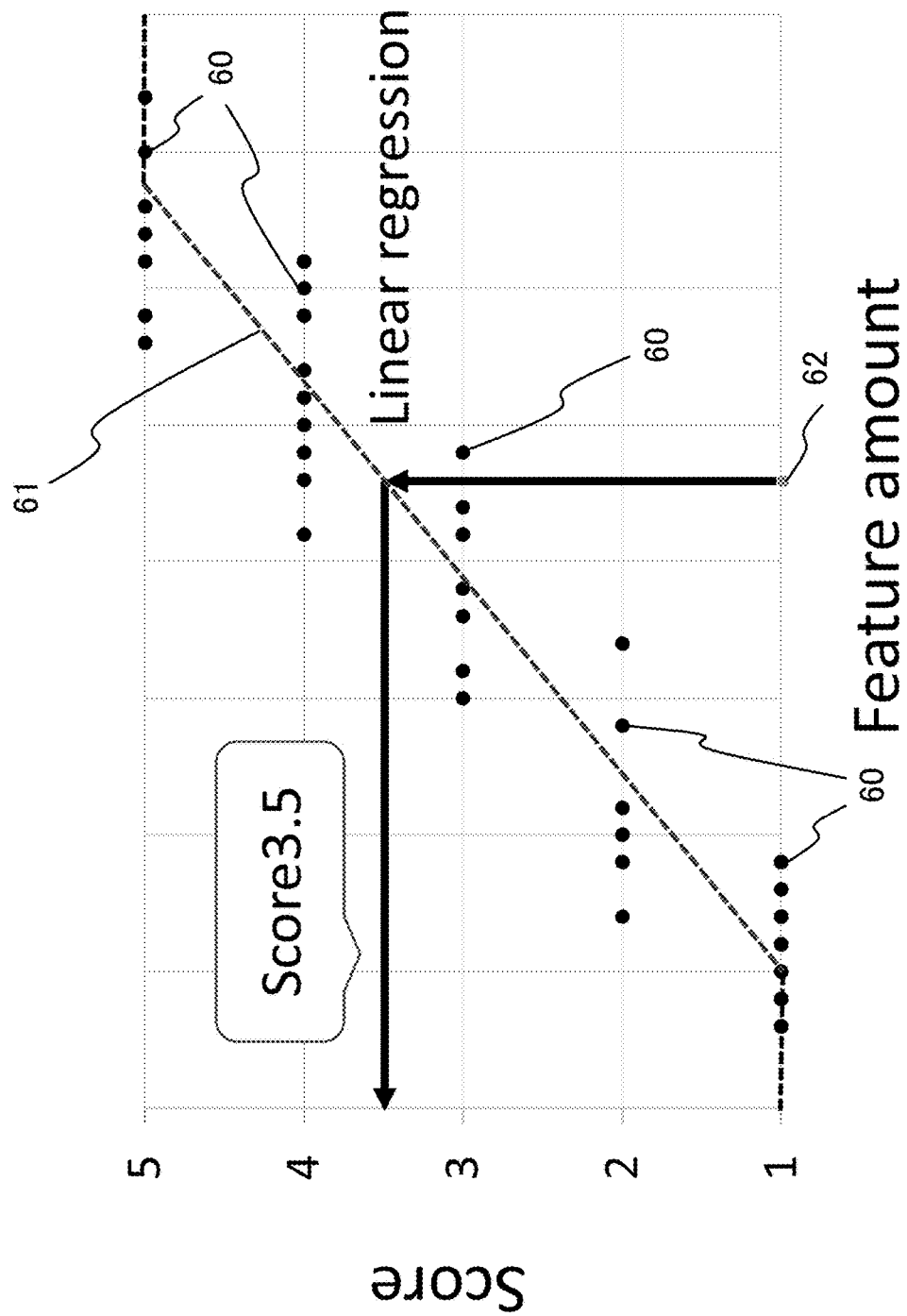
FIG. 8 is a diagram illustrating an example of a linear regression model.

FIG. 8 is a diagram illustrating an example of a linear regression model. It is assumed that the linear regression model 61 has been calculated in advance by performing a regression analysis with each feature amount 60 as a predictor variable and a score as a criterion variable. Note that it is assumed that the scores given in advance by a veterinarian or a dairyman is used. Thus, for example, the score for the feature amount 62 can be calculated as 3.5 according to the linear regression model 61. In a case where scores are expressed in 5 stages, the calculated score may be rounded off.

According to such a method, the score calculation unit 13 calculates a rumen fill score according to at least one of the first to third feature amounts. In addition, the score calculation unit 13 calculates a locomotion score according to at least one of the fourth to eighth feature amounts. In addition, the score calculation unit 13 calculates a body condition score according to at least one of the ninth and the tenth feature amounts.

Note that the score calculation unit 13 may classify a cow into a class corresponding to any of the above scores according to any one of the above feature amounts. For example, the feature amount extraction unit 12 may classify a cow into one of class 1 having the locomotion score of 1 and class 2 having the locomotion score of 2 or more.

That is, in the present disclosure, calculation of a score includes classification into a class corresponding to the score.

EXPERIMENTAL RESULTS

Next, experimental results on calculation of a locomotion score using the health condition estimation device 10 will be described.

Here, it is assumed that the feature amount extraction unit 12 calculates the above eighth feature amount (gait feature) from the group of three-dimensional coordinates of a target cow, acquired by the three-dimensional coordinates acquisition unit 11. Specifically, the feature amount extraction unit 12 calculates an average silhouette feature which is one of the two-dimensional silhouette features, and an average depth feature which is one of the three-dimensional silhouette features, from among the gait features described above.

In addition, the score calculation unit 13 uses a SVM (Support Vector Machine) to classify the locomotion score of the target cow into one of 1 and 2 or greater by using the feature amounts extracted by the feature amount extraction unit 12.

Figure 9:
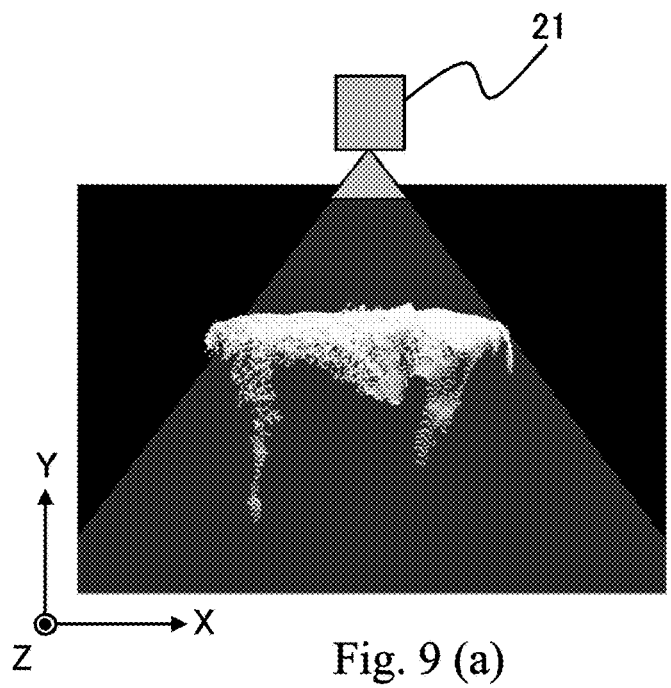
FIG. 9 (a) is a view illustrating an example of a group of three-dimensional coordinates of a cow acquired by a three-dimensional coordinates acquisition unit 11, FIG. 9 (b) is a view illustrating an average depth feature, and FIG. 9 (c) illustrates a silhouette feature.
Figure 9:
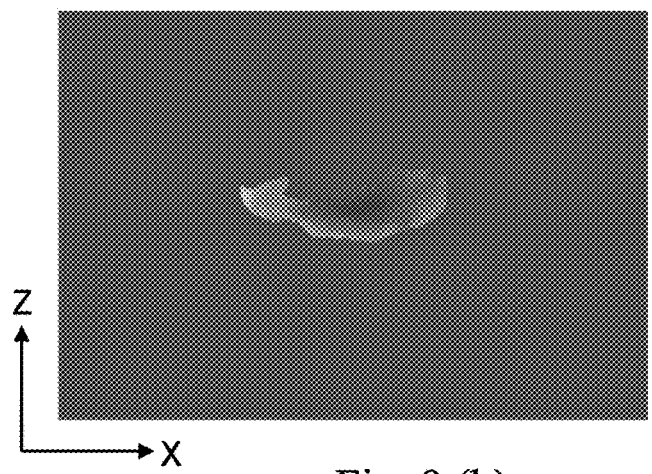
Figure 9:
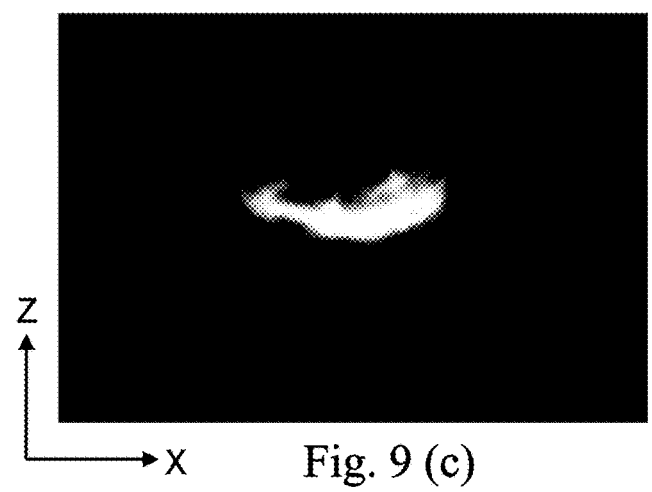

FIG. 9 (*a*) is a view illustrating an example of a group of three-dimensional coordinates of a cow acquired by the three-dimensional coordinates acquisition unit 11. In FIG. 9 (*a*), the three-dimensional coordinates of the cow are indicated by whitish points. FIG. 9 (*a*) is a view of the cow as viewed from a side. Here, it is assumed that the three-dimensional coordinates acquisition unit 11 acquires, for each cow, a group of three-dimensional coordinates corresponding to one walking cycle from a predetermined database.

The feature amount extraction unit 12 performs coordinate transformation of the group of three-dimensional coordinates illustrated in FIG. 9 (*a*) to obtain depth data from a camera 21 virtually installed above the cow to the back surface of the cow assuming that the cow is imaged by the camera 21. The feature amount extraction unit 12 calculates the average depth of respective points on the back surface of the cow from the depth data for one walking cycle. FIG. 9 (*b*) is a view illustrating an average depth feature, and each pixel disposed near the center of FIG. 9 (*b*) indicates the average depth of each point on the back surface of the cow. Except for the background part other than the cow, as a point is whiter, the distance from the camera 21 is greater. Expression 6 is an expression for calculating the average depth. Here, $\mu(x, z)$ represents the average depth of the coordinates $(x, z)$, $d_m(x, z)$ represents the depth data at the coordinates $(x, z)$ of the m-th image, and $M(x, z)$ represents the number of groups of three-dimensional coordinate groups in which depth data is observed at the coordinates $(x, z)$ in the groups of three-dimensional coordinates for one walking cycle.

[Mathematical Expression 3]

$$\mu(x, z) = \frac{1}{M(x, z)} \sum_{m=1}^{M} d_m(x, z) \qquad \text{(Expression 6)}$$

The average depth feature can represent the degree of curve of the back.

In addition, the feature amount extraction unit 12 performs coordinate transformation of the group of three-dimensional coordinates illustrated in FIG. 9 (*a*) to obtain a silhouette image of the cow obtained when it is assumed that the cow is imaged by the camera 21 virtually installed above the cow. The feature amount extraction unit 12 calculates the appearance probability of the silhouette for each pixel from the silhouette images in one walking cycle. FIG. 9 (*c*) is a view illustrating a silhouette feature, and each pixel disposed near the center of FIG. 9 (*c*) indicates the appearance probability of the silhouette of the cow. Except for the background part other than the cow, as a point is whiter, the appearance probability of the silhouette image is greater. Expression 7 is an expression for calculating the appearance probability of the silhouette. Here, $P(x, z)$ represents the appearance probability of the silhouette at the coordinates $(x, z)$, N represents the number of groups of three-dimensional coordinates for one walking cycle, and $M(x, z)$ is as described above.

[Mathematical Expression 4]

$$P(x, z) = \frac{M(x, z)}{N} \qquad \text{(Expression 7)}$$

The score calculation unit 13 uses the learned SVM to classify the average depth feature or the silhouette feature extracted by the feature amount extraction unit 12 into one of two classes. For example, the score calculation unit 13 performs classification into one of class 1 having the locomotion score of 1 and class 2 having the locomotion score of 2 or more.

Note that learning of the SVM is performed using the locomotion score given by a dairyman and the average depth feature or the average silhouette feature extracted from the group of three-dimensional coordinates for learning. At that time, each feature amount is multidimensional data. For this reason, dimensional compression using principal component analysis is performed before learning. The dimensionally compressed data is learned as the average depth feature or the average silhouette feature, and an SVM is obtained as a two-class classifier.

FIG. 10 illustrates the results of classification of locomotion scores into classes by using the SVM. Here, classification experiments are performed on a total of 523 sequences of groups of three-dimensional coordinates for 16 cows. The first column of the table illustrated in FIG. 10 illustrates the feature amounts and the kernels of the SVM used for classification into classes. The "correct answer rate (%)" in the second column indicates the correct answer rate (%) of the overall classification into classes. "Correct answer rate (%) for class 1" in the third column indicates the ratio of cows correctly classified into class 1 to the cows supposed to be classified into class 1. "Correct answer rate (%) for class 2" in the fourth column indicates the ratio of cows correctly classified into class 2 to the cows supposed to be classified into class 2. In addition, in the table illustrated in FIG. 10, a thick frame indicates the highest correct answer rate in each column.

According to this table, it can be seen that the correct answer rate is higher when a RBF (Radial Basis Function) kernel is used as the kernel of the SVM than when a linear kernel is used. In addition, it can be seen that the SVM using the linear kernel is not suitable for classification, but the correct answer rate of the SVM using the RBF kernel is 90% or higher. In particular, in a case where average silhouette features are classified by the SVM using the RBF kernel, it can be seen that the average silhouette features can be classified with the correct answer rate of nearly 100%.

Note that as a conventional method, there is a method disclosed in Non Patent Literature 8. In the conventional method, the curved degree of the back of a cow is used as a feature. Specifically, an ellipse is fitted to the position of the backbone of a cow, and the positional relationship of the backbone is represented by an angle or a length to be used as a feature amount. According to the conventional method disclosed in Non Patent Literature 8, classification into two classes, that is, a class with the locomotion score of 2 or less and a class with a locomotion score of 3 or more is performed, and accuracy of about 90% is obtained.

Non Patent Literature 8: Viazzi et al., "Comparison of a three-dimensional and two-dimensional camera system for automated measurement of back posture in dairy cows", Computers and Electronics in Agriculture, 139-147, 2014.

With reference to the average depth similar to the feature amount used in the conventional method, from the result illustrated in FIG. 10, it can be considered that the correct answer rate of classification into class 2 with the locomotion score of 2 or more is about 70%. In contrast, as described above, in the present embodiment, by using the silhouette feature taking movement into consideration as a feature amount, the correct answer rate of classification into class 2 with the locomotion score of 2 or more is about 97%.

Therefore, according to the health condition estimation device 10 disclosed in the present embodiment, it is found that classification into classes by using a locomotion score can be accurately performed.

Effects of Embodiment 1

As described above, the health condition estimation device 10 according to Embodiment 1 extracts a feature amount from a group of three-dimensional coordinates representing the three-dimensional shape of a cow and calculates a score that indicates the health condition of the cow according to the feature amount. The group of three-dimensional coordinates can be obtained from the distance image. Therefore, even if the posture of a cow is inclined to some degree with respect to a camera, it is possible to calculate the accurate three-dimensional coordinates of the cow from the distance image. Therefore, it is possible to accurately estimate the health condition of a cow without performing accurate positioning of the cow.

In a case where the rumen area does not sink, the curvature of the area becomes relatively small; however, in a case where the rumen area sinks, the curvature becomes relatively great. Therefore, by using the histogram of the curvature represented by the first feature amount as a feature amount indicating the degree of sinking of the rumen, it is possible to accurately calculate the rumen fill score.

In addition, in a case where the rumen area does not sink, the distance between the rumen area and the plane fitted to the rumen area becomes relatively small; however, in a case where the rumen area sinks, the distance becomes relatively great. Therefore, by using the distance represented by the second feature amount as the feature amount indicating the degree of sinking of the rumen, it is possible to accurately calculate the rumen fill score.

In addition, in a case where the rumen area does not sink, the volume of the space between the convex hull surrounding the rumen area and the rumen area, represented by the third feature amount becomes relatively small; however, in a case where the rumen area sinks, the volume becomes relatively large. Therefore, by using the volume as the feature amount indicating the degree of sinking of the rumen, it is possible to accurately calculate the rumen fill score.

In addition, the back line of a cow has a curved shape. Therefore, as represented by the fourth feature amount, the parameter of the curve obtained by fitting the curve to the back line can be used as the feature amount of the back line. Therefore, it is possible to accurately calculate the locomotion score.

In addition, in the case of a cow whose backbone is curved, the back line is also curved. Therefore, the shift amount from a straight line, represented by the fifth feature amount becomes relatively great. In contrast, in the case of a cow whose backbone is not curved, the back line is not curved so much. Therefore, the shift amount becomes relatively small. Therefore, it is possible to accurately calculate the locomotion score by using the fifth feature amount as the feature amount of the back line.

In addition, by using the sixth feature amount, for example, the manner of walking inclined to the left such that the left shoulder is located lower than the right shoulder can be represented as a feature amount. Therefore, it is possible to accurately calculate the locomotion score of a cow according to the sixth feature amount.

In addition, by using the seventh feature amount, for example, the step length, the amount of protrusion of a leg from the width of the trunk, or the like of a cow can be quantified and expressed as a feature amount. Therefore, it is possible to accurately calculate the locomotion score of a cow according to the seventh feature amount.

In addition, by using the eight feature amount, it is possible to express a walking manner of a cow or the like as a gait feature amount. Therefore, it is possible to accurately calculate the locomotion score of a cow according to such a gait feature amount.

In addition, by using the ninth or tenth feature amount, for example, the maximum width of the body, the height of the backbone along the body, or the like of a cow can be quantified and expressed as a feature amount. Therefore, it is possible to accurately calculate the body condition score of a cow according to the above feature amount.

Modification of Embodiment 1

Next, a modification of Embodiment 1 will be described.

The present modification is different from Embodiment 1 in the method of specifying the positions of the rumen area, the back line, and the like. In other words, in the present modification, the positions of the rumen area, the back line, and the like are specified by aligning the group of three-dimensional coordinates of the cow to be focused on and a predetermined model of groups of three-dimensional coordinates of cows.

Figure 11:
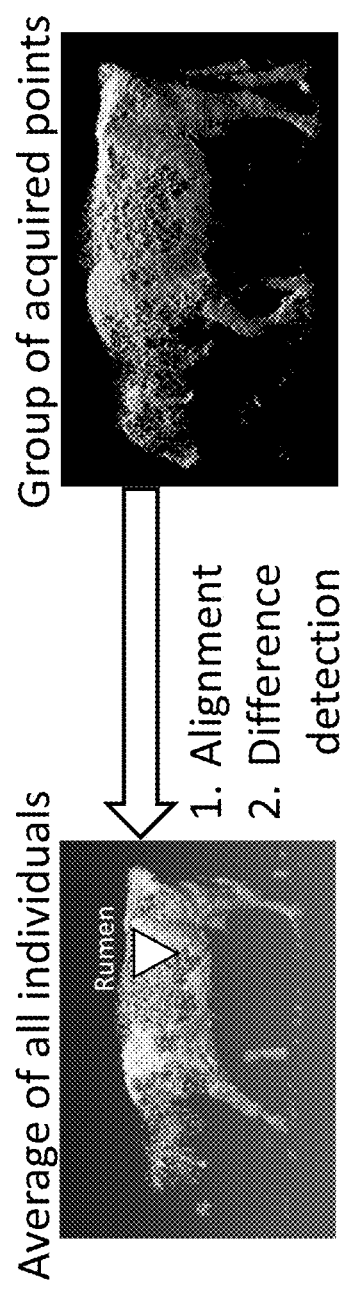
FIGS. 11 (a) and 11 (b) are views for explaining a method of specifying a rumen area by collation with a standard model.

In other words, it is assumed that a group of three-dimensional coordinates has been acquired for each of a plurality of cows, and that groups of three-dimensional coordinates of the plurality of cows are aligned by using the ICP method, a Coherent Point Drift method, or the like. In addition, it is assumed that the average shape of the trunk parts of the cows obtained from the alignment result is prepared in advance as a cow standard model. Further, it is assumed that in the standard model, part information is tagged on the rumen area or the like. FIG. 11 (a) illustrates an example of the standard model and the tagged rumen area.

The feature amount extraction unit 12 aligns the group of three-dimensional coordinates of a target cow to be subjected to feature extraction illustrated in FIG. 11 (b) and the standard model illustrated in FIG. 11 (a), and specifies the positions of the rumen area, the back line, and the like of the target cow by specifying the positions corresponding to the tagged rumen area and the back line of the standard model.

Embodiment 2

In Embodiment 1, the scores of a cow are calculated by using regression analysis. In Embodiment 2, a standard model prepared for each score is collated with a group of three-dimensional coordinates of a cow to be subjected to score calculation to calculate the scores of the cow.

Figure 12:
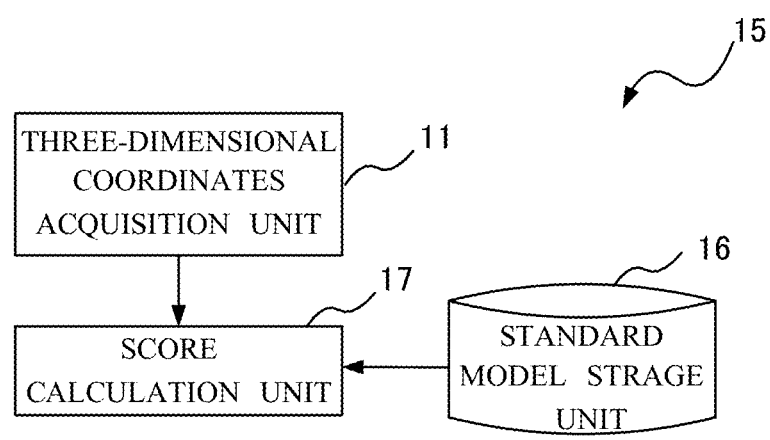
FIG. 12 is a block diagram illustrating a functional configuration of a health condition estimation device according to Embodiment 2 of the present invention.

FIG. 12 is a block diagram illustrating a functional configuration of a health condition estimation device according to Embodiment 2 of the present invention.

A health condition estimation device 15 is a device which estimates the health condition of a cow and includes a three-dimensional coordinates acquisition unit 11, a standard model storage unit 16, and a score calculation unit 17.

Similarly to Embodiment 1, the three-dimensional coordinates acquisition unit 11 acquires a group of three-dimensional coordinates representing the three-dimensional shape of a cow extracted from a distance image of the cow.

The standard model storage unit 16 is a storage device which stores a standard model database representing a standard model of a cow for each score, and is configured of a storage device such as an HDD (Hard Disk Drive) and a RAM (Random Access Memory).

Figure 13:
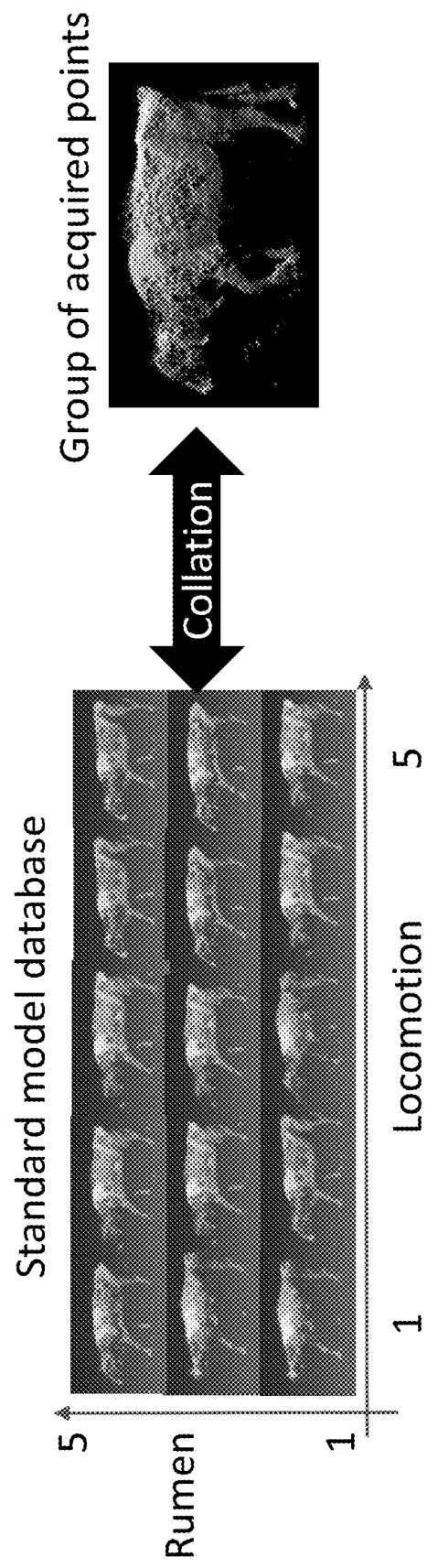
FIGS. 13 (a) and 13 (b) are diagrams for explaining a method of calculating a rumen fill score and a locomotion score using a standard model database.

FIG. 13 (a) is a diagram illustrating an example of a standard model database. A standard model is stored for each combination of scores when the horizontal axis indicates a locomotion score and the vertical axis indicates a rumen fill score. That is, locomotion scores and rumen fill scores are given by a veterinarian or a dairyman for each of a plurality of cows. It is assumed that for each combination of the locomotion score and the rumen fill score, groups of three-dimensional coordinates of the cows having the combination of scores are aligned by using the ICP method, the Coherent Point Drift method or the like, and that the average shape of the trunk parts of the cows obtained from the alignment result is prepared in advance as a cow standard model.

The score calculation unit 17 aligns the group of three-dimensional coordinates of a target cow to be subjected to score calculation as illustrated in FIG. 13 (b) and each standard model included in the standard model database illustrated in FIG. 13 (a) so as to associate the group of three-dimensional coordinates with each standard model. The score calculation unit 17 selects a standard model with the smallest residual error between the associated distances as a result of the alignment, and calculates the combination of the locomotion score and the rumen fill score corresponding to the selected standard model as the locomotion score and the rumen fill score of the target cow.

Note that in the standard model database illustrated in FIG. 13 (a), a standard model is prepared for each combination of the locomotion score and the rumen fill score; however, a standard model may be prepared for each combination of the locomotion score, the rumen fill score, and a body condition score by further adding the body condition score. In addition, a standard model may be prepared for each combination of the body condition score and the locomotion score or the rumen fill score.

In addition, the cow standard model may be time-series data of a group of three-dimensional coordinates.

This makes it possible to express the walking state of a cow in more detail.

As described above, according to Embodiment 2, the standard model closest to the group of three-dimensional coordinates acquired by the three-dimensional coordinates acquisition unit 11 can be selected from the standard model database. In addition, the score corresponding to the selected standard model can be used as the score of the cow. The group of three-dimensional coordinates can be obtained from the distance image. Therefore, even if the posture of a cow is inclined to some degree with respect to a camera, it is possible to calculate the accurate three-dimensional coordinates of the cow from the distance image. Therefore, it is possible to accurately estimate the health condition of a cow without performing accurate positioning of the cow.

Specifically, each of the health condition estimation devices 10 and 15 described above may be configured as a computer system including a microprocessor, a ROM, a RAM, a hard disk drive, a display unit, a keyboard, a mouse, and the like. A computer program is stored in the RAM or the hard disk drive. The microprocessor operating according to the computer program enables each device to achieve its function. Here, the computer program is configured by combining a plurality of instruction codes indicating instructions to the computer in order to achieve a predetermined function.

Further, some or all of the constituent elements constituting each of the above-described devices may be configured of one system LSI (Large Scale Integration).

In addition, the present invention may be the methods described above. In addition, the present invention may be a computer program realizing these methods by a computer.

In addition, each step included in the program may be executed by a plurality of computers.

Further, the embodiments and the modification described above may be combined.

It should be understood that the embodiments disclosed herein are examples in all respects and are not restrictive. The scope of the present invention is defined not by the above meaning but by the claims, and all modifications within the meaning and the scope of the claims and equivalent thereof are intended to be included.

INDUSTRIAL APPLICABILITY

The present invention can be applied to a health condition estimation device or the like which estimates the health condition of a cow.

REFERENCE SIGNS LIST 10, 15 Health condition estimation device
11 Three-dimensional coordinates acquisition unit
12 Feature amount extraction unit
13, 17 Score calculation unit
16 Standard model storage unit
FIG. 1
11 Three-dimensional coordinates acquisition unit
12 Feature amount extraction unit
13 Score calculation unit
FIG. 2
1 Trunk
FIG. 4(b)
1 Frequency
2 Curvature
FIGS. 6(a) to 6(c)
1 Cross-section
2 Inclination of back
3 Upward to the right
4 Inclination
5 Upward to the left
6 Trouble in right leg
7 Time
FIGS. 7(a) to 7(b)
1 Appearance of backbone
2 Width of body
3 Position of backbone
FIG. 8
1 Score
2 Feature amount
3 Linear regression
FIG. 10
1 Feature amount (kernel)
2 Average depth
3 Average silhouette
4 Correct answer rate (%)
5 Correct answer rate with respect to class 1(%)
6 Correct answer rate with respect to class 2(%)
FIGS. 11(a) to 11(b)
1 Average of all individuals
2 1. Alignment
3 2. Difference detection
4 Group of acquired points FIG. 12
11 Three-dimensional coordinates acquisition unit
16 Standard model storage unit
17 Score calculation unit
FIG. 13
1 Rumen
2 Standard model database
3 Locomotion
4 Group of acquired points
5 Collation

The invention claimed is:

1. A health condition estimation device estimating a health condition of a cow, the device comprising:
   a three-dimensional coordinates acquisition unit which acquires a group of three-dimensional coordinates representing a three-dimensional shape of a cow extracted from a distance image of the cow;
   a feature amount extraction unit which extracts a feature amount of the cow, according to the group of three-dimensional coordinates acquired by the three-dimensional coordinates acquisition unit; and
   a score calculation unit which calculates a score that indicates a health condition of the cow, according to the feature amount extracted by the feature amount extraction unit;
   wherein the feature amount extraction unit extracts a feature amount indicating the temporal change of a walking state of the cow according to the time-series group of three-dimensional coordinates, and
   wherein the score calculation unit calculates a locomotion score of the cow according to the feature amount of the walking state of the cow extracted by the feature amount extraction unit.

2. The health condition estimation device according to claim 1,
   wherein the feature amount extraction unit extracts a feature amount that indicates a degree of sinking of a rumen of the cow, according a group of three-dimensional coordinates of a rumen area in the group of three-dimensional coordinates acquired by the three-dimensional coordinates acquisition unit, the rumen area being an area on a body surface of the cow proximal to the rumen, and
   wherein the score calculation unit calculates a rumen fill score of the cow, according to the feature amount extracted by the feature amount extraction unit and indicating the degree of sinking of the rumen.

3. The health condition estimation device according to claim 2, wherein the feature amount extraction unit extracts a histogram of a curvature in the rumen area as the feature amount indicating the degree of sinking of the rumen, according to the group of three-dimensional coordinates of the rumen area.

4. The health condition estimation device according to claim 2, wherein the feature amount extraction unit extracts a distance between the rumen area and a predetermined plane applied to the rumen area as the feature amount indicating the degree of sinking of the rumen, according to the group of three-dimensional coordinates of the rumen area.

5. The health condition estimation device according to claim 2, wherein the feature amount extraction unit extract a volume of a space between a convex hull surrounding the rumen area and the rumen area as the feature amount indicating the degree of sinking of the rumen, according to the group of three-dimensional coordinates of the rumen area.

6. The health condition estimation device according to claim 2,
   wherein the three-dimensional coordinates acquisition unit acquires a time-series group of three-dimensional coordinates from time-series distance images of the cow, and
   wherein the feature amount extraction unit extracts a feature amount indicating a degree of sinking of the rumen obtained when the degree of sinking of the rumen is greatest, according to a time-series group of three-dimensional coordinates of the rumen area.

7. The health condition estimation device according to claim 1,
   wherein the feature amount extraction unit detects a back line of the cow, according to the group of three-dimensional coordinates acquired by the three-dimensional coordinates acquisition unit, and extracts as a feature amount of the back line a parameter of a predetermined curve obtained by fitting the predetermined curve to the back line which is detected, and
   wherein the score calculation unit calculates a locomotion score of the cow according to the feature amount of the back line extracted by the feature amount extraction unit.

8. The health condition estimation device according to claim 1,
   wherein the feature amount extraction unit detects a back line of the cow, according to the group of three-dimensional coordinates acquired by the three-dimensional coordinates acquisition unit, and extracts as a feature amount of the back line a shift amount of the back line which is detected, from a predetermined line, and
   wherein the score calculation unit calculates a locomotion score of the cow according to the feature amount of the back line extracted by the feature amount extraction unit.

9. The health condition estimation device according to claim 1, wherein the feature amount extraction unit extracts, as the feature amount, a value indicating variation in a degree of inclination in a right-left direction during walking of the cow, according to the time-series group of three-dimensional coordinates.

10. The health condition estimation device according to claim 1, wherein the feature amount extraction unit extracts, as the feature amount, a value indicating movement of a leg during walking of the cow, according to the time-series group of three-dimensional coordinates.

11. The health condition estimation device according to claim 1, wherein the feature amount extraction unit extracts a gait feature amount of the cow as the feature amount, according to the time-series group of three-dimensional coordinates.

12. The health condition estimation device according to claim 1,
   wherein the feature amount extraction unit extracts a feature amount indicating one of a width of a body and a position of a backbone of the cow, according to the group of three-dimensional coordinates acquired by the three-dimensional coordinates acquisition unit, and
   wherein the score calculation unit calculates a body condition score of the cow according to the feature amount indicating one of the width of the body and the position of the backbone of the cow, the feature amount being extracted by the feature amount extraction unit.

13. A health condition estimation device estimating a health condition of a cow, the device comprising:

a three-dimensional coordinates acquisition unit which acquires a time-series group of three-dimensional coordinates representing a time-series three-dimensional shape of a cow extracted from a time-series distance image of the cow; and a score calculation unit which calculates a combination of scores of the cow corresponding to the time-series group of three-dimensional coordinates acquired by the three-dimensional coordinates acquisition unit by associating a standard model of a time-series group of three-dimensional coordinates of the cow classified for each combination of a locomotion score and at least one of a rumen fill score and a body condition score with the time-series group of three-dimensional coordinates acquired by the three-dimensional coordinates acquisition unit.

* * * * *